(12) United States Patent
Falotico et al.

(10) Patent No.: US 7,195,640 B2
(45) Date of Patent: Mar. 27, 2007

(54) COATED MEDICAL DEVICES FOR THE TREATMENT OF VULNERABLE PLAQUE

(75) Inventors: Robert Falotico, Belle Mead, NJ (US); John Spaltro, Asbury, NJ (US)

(73) Assignee: Cordis Corporation, Miami Lakes, FL (US)

(*) Notice: Subject to any disclaimer, the term of this patent is extended or adjusted under 35 U.S.C. 154(b) by 313 days.

(21) Appl. No.: 10/122,978

(22) Filed: Apr. 15, 2002

(65) Prior Publication Data

US 2003/0060877 A1     Mar. 27, 2003

Related U.S. Application Data

(63) Continuation-in-part of application No. 09/962,496, filed on Sep. 25, 2001, now abandoned.

(51) Int. Cl.
*A61F 2/06* (2006.01)
(52) U.S. Cl. .................... 623/1.42; 623/1.46; 623/1.15
(58) Field of Classification Search ............ 604/95.03, 604/96.01, 101.02, 103.02, 51–53, 500, 890.1, 604/891.1; 623/11, 1.42–1.48, 1.16, 1.15; 512/291, 56, 378, 466, 824, 521, 18, 456, 512/763, 44, 2, 93.2, 96.4; 424/122, 423–424, 424/290.22
See application file for complete search history.

(56) References Cited

U.S. PATENT DOCUMENTS

| | | | |
|---|---|---|---|
| 3,585,707 A | 6/1971 | Stevens | ...................... 29/426.2 |
| 3,657,744 A | 4/1972 | Ersek | |
| 3,929,992 A | 12/1975 | Seghal et al. | ................ 424/122 |
| 3,932,627 A | 1/1976 | Margraf | |
| 3,959,078 A | 5/1976 | Guire | ........................... 530/350 |
| 4,292,965 A | 10/1981 | Nash et al. | |
| 4,366,819 A | 1/1983 | Kaster | ......................... 606/153 |

(Continued)

FOREIGN PATENT DOCUMENTS

DE       3205942 A1     9/1983

(Continued)

OTHER PUBLICATIONS

European Search Report dated Sep. 22, 2003 for corresponding Appln. No. EP 03 25 2350.

(Continued)

*Primary Examiner*—Henry Bennett
*Assistant Examiner*—Camtu Nguyen

(57) ABSTRACT

Medical devices, and in particular implantable medical devices, may be coated to minimize or substantially eliminate a biological organism's reaction to the introduction of the medical device to the organism. The medical devices may be coated with any number of biocompatible materials. Therapeutic drugs, agents or compounds may be mixed with the biocompatible materials and affixed to at least a portion of the medical device. In addition to reducing or substantially eliminating a biological organism's reaction to the introduction of the medical device to the organism, the medical device in combination with one or more therapeutic drugs, agents and/or compounds may be utilized to treat various vascular diseases, for example, restenosis and vulnerable plaque. In the case of vulnerable plaque, one or more drugs, agents or compounds may be utilized to treat the various aspects of vulnerable plaque and these drugs, agents and/or compounds may be released with a given release profile for the most effective treatment. Various materials and coating methodologies may be utilized to maintain the drugs, agents or compounds on the medical device until delivered and positioned.

30 Claims, 20 Drawing Sheets

U.S. PATENT DOCUMENTS

| | | | |
|---|---|---|---|
| 4,368,736 A | 1/1983 | Kaster | 606/153 |
| 4,441,216 A | 4/1984 | Ionescu et al. | |
| 4,503,569 A | 3/1985 | Dotter | |
| 4,553,545 A | 11/1985 | Maass et al. | |
| 4,580,568 A | 4/1986 | Gianturco | |
| 4,613,665 A | 9/1986 | Larm | |
| 4,624,257 A | 11/1986 | Berggren et al. | 606/153 |
| 4,655,771 A | 4/1987 | Wallsten | |
| 4,722,906 A | 2/1988 | Guire | 436/501 |
| 4,733,665 A | 3/1988 | Palmaz | |
| 4,739,665 A | 4/1988 | Nordvall | 73/862.08 |
| 4,739,762 A | 4/1988 | Palmaz | |
| 4,776,337 A | 10/1988 | Palmaz | |
| 4,800,882 A | 1/1989 | Gianturco | |
| 4,810,784 A | 3/1989 | Larm | 536/20 |
| 4,856,516 A | 8/1989 | Hillstead | |
| 4,872,867 A | 10/1989 | Joh | |
| 4,886,062 A | 12/1989 | Wiktor | |
| 4,907,336 A | 3/1990 | Gianturco | |
| 4,916,193 A | 4/1990 | Tang et al. | |
| 4,917,090 A | 4/1990 | Berggren et al. | 606/153 |
| 4,917,091 A | 4/1990 | Berggren et al. | 606/153 |
| 4,954,126 A | 9/1990 | Wallsten | |
| 4,969,458 A | 11/1990 | Wiktor | |
| 4,990,131 A | 2/1991 | Dardik | |
| 4,990,155 A | 2/1991 | Wilkoff | |
| 4,994,071 A | 2/1991 | MacGregor | |
| 5,015,253 A | 5/1991 | MacGregor | |
| 5,035,706 A | 7/1991 | Giantureo | |
| 5,041,100 A | 8/1991 | Rowland et al. | |
| 5,041,126 A | 8/1991 | Gianturco | |
| 5,045,072 A | 9/1991 | Castillo et al. | 604/529 |
| 5,049,132 A | 9/1991 | Shaffer et al. | |
| 5,049,403 A | 9/1991 | Larm et al. | 427/2.1 |
| 5,053,048 A | 10/1991 | Pinchuk | |
| 5,061,275 A | 10/1991 | Wallsten et al. | |
| 5,061,750 A | 10/1991 | Feijen et al. | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,116,365 A | 5/1992 | Hillstead | |
| 5,122,154 A | 6/1992 | Rhodes | |
| 5,131,908 A | 7/1992 | Dardik et al. | |
| 5,133,732 A | 7/1992 | Wiktor | |
| 5,134,192 A | 7/1992 | Feijen et al. | |
| 5,135,536 A | 8/1992 | Hillstead | |
| 5,163,952 A | 11/1992 | Froix | |
| 5,163,958 A | 11/1992 | Pinchuk | |
| 5,171,262 A | 12/1992 | MacGregor | |
| 5,176,660 A | 1/1993 | Truckai | |
| 5,178,618 A | 1/1993 | Kandarpa | |
| 5,180,366 A | 1/1993 | Woods | |
| 5,182,317 A | 1/1993 | Winters et al. | |
| 5,185,408 A | 2/1993 | Tang et al. | |
| 5,192,307 A | 3/1993 | Wall | |
| 5,195,984 A | 3/1993 | Shalz | |
| 5,213,576 A | 5/1993 | Abiuso et al. | |
| 5,217,483 A | 6/1993 | Tower | |
| 5,222,971 A | 6/1993 | Willard et al. | |
| 5,226,913 A | 7/1993 | Pinchuk | |
| 5,229,172 A | 7/1993 | Cahalan et al. | 427/536 |
| 5,234,456 A | 8/1993 | Silvestrini | |
| 5,246,445 A | 9/1993 | Yachia et al. | |
| 5,254,107 A | 10/1993 | Soltesz | 604/525 |
| 5,258,020 A | 11/1993 | Froix | |
| 5,258,021 A | 11/1993 | Duran | |
| 5,262,451 A | 11/1993 | Winters et al. | |
| 5,266,073 A | 11/1993 | Wall | |
| 5,272,012 A | 12/1993 | Opolski | 428/423.1 |
| 5,275,622 A | 1/1994 | Lazarus et al. | |
| 5,282,823 A | 2/1994 | Schwartz et al. | |
| 5,282,824 A | 2/1994 | Gianturco | |
| 5,283,257 A | 2/1994 | Gregory et al. | |
| 5,288,711 A | 2/1994 | Mitchell et al. | |
| 5,290,305 A | 3/1994 | Inoue | |
| 5,292,331 A | 3/1994 | Boneau | |
| 5,292,802 A | 3/1994 | Rhee et al. | |
| 5,304,121 A | 4/1994 | Sahatjian | |
| 5,304,200 A | 4/1994 | Spaulding | |
| 5,306,250 A | 4/1994 | March et al. | |
| 5,308,641 A | 5/1994 | Cahalan et al. | 427/2.1 |
| 5,308,862 A | 5/1994 | Ohlstein | |
| 5,308,889 A | 5/1994 | Rhee et al. | |
| 5,314,444 A | 5/1994 | Gianturco | |
| 5,314,472 A | 5/1994 | Fontaine | |
| 5,328,471 A | 7/1994 | Slepian | |
| 5,334,301 A | 8/1994 | Heinke et al. | |
| 5,336,518 A | 8/1994 | Narayanan et al. | |
| 5,338,770 A | 8/1994 | Winters et al. | |
| 5,342,348 A | 8/1994 | Kaplan | |
| 5,342,387 A | 8/1994 | Summers | |
| 5,342,621 A | 8/1994 | Eury | |
| 5,350,800 A | 9/1994 | Verhoeven et al. | 525/54.2 |
| 5,354,257 A | 10/1994 | Roubin et al. | |
| 5,354,308 A | 10/1994 | Simon et al. | |
| 5,356,433 A | 10/1994 | Rowland et al. | |
| 5,366,504 A | 11/1994 | Andersen et al. | |
| 5,368,566 A | 11/1994 | Crocker | |
| 5,370,683 A | 12/1994 | Fontaine | |
| 5,370,691 A | 12/1994 | Samson | |
| 5,375,612 A | 12/1994 | Cottenceau et al. | |
| 5,376,112 A | 12/1994 | Duran | |
| 5,380,299 A | 1/1995 | Fearnot et al. | |
| 5,382,261 A | 1/1995 | Palmaz | |
| 5,383,928 A | 1/1995 | Scott et al. | |
| 5,387,235 A | 2/1995 | Chuter | |
| 5,389,106 A | 2/1995 | Tower | |
| 5,393,772 A | 2/1995 | Yue et al. | |
| 5,395,390 A | 3/1995 | Simon et al. | |
| 5,397,355 A | 3/1995 | Marin et al. | |
| 5,403,341 A | 4/1995 | Solar | |
| 5,405,377 A | 4/1995 | Cragg | |
| 5,409,696 A | 4/1995 | Narayanan et al. | |
| 5,411,549 A | 5/1995 | Peters | |
| 5,415,619 A | 5/1995 | Lee et al. | |
| 5,415,938 A | 5/1995 | Cahalan et al. | 428/409 |
| 5,419,760 A | 5/1995 | Narciso, Jr. | |
| D359,802 S | 6/1995 | Fontaine | |
| 5,421,955 A | 6/1995 | Lau | |
| 5,423,885 A | 6/1995 | Williams | |
| 5,429,618 A | 7/1995 | Keogh | |
| 5,429,634 A | 7/1995 | Narcisco | |
| 5,439,446 A | 8/1995 | Barry | |
| 5,441,515 A | 8/1995 | Khosravi et al. | |
| 5,441,516 A | 8/1995 | Wang et al. | |
| 5,441,947 A | 8/1995 | Dodge et al. | |
| 5,443,458 A | 8/1995 | Eury | |
| 5,443,477 A | 8/1995 | Marin et al. | |
| 5,443,496 A | 8/1995 | Schwartz et al. | |
| 5,443,498 A | 8/1995 | Fontaine | |
| 5,443,500 A | 8/1995 | Sigwart | |
| 5,447,724 A | 9/1995 | Heimus et al. | |
| 5,449,372 A | 9/1995 | Schmaltz et al. | |
| 5,449,373 A | 9/1995 | Pinchasik et al. | |
| 5,449,382 A | 9/1995 | Dayton | |
| 5,464,450 A | 11/1995 | Buscemi et al. | |
| 5,464,650 A | 11/1995 | Berg et al. | |
| 5,486,357 A | 1/1996 | Narayanan | |
| 5,496,365 A | 3/1996 | Sgro | |
| 5,500,013 A | 3/1996 | Buscemi et al. | |
| 5,510,077 A | 4/1996 | Dinh et al. | |
| 5,516,781 A * | 5/1996 | Morris et al. | 514/291 |
| 5,523,092 A | 6/1996 | Hanson et al. | |

| | | | | | |
|---|---|---|---|---|---|
| 5,527,354 A | 6/1996 | Fontaine et al. | 5,792,772 A | 8/1998 | Bianco et al. |
| 5,545,208 A | 8/1996 | Wolff et al. | 5,798,372 A | 8/1998 | Davies et al. |
| 5,551,954 A | 9/1996 | Buscemi et al. | 5,799,384 A | 9/1998 | Schwartz et al. |
| 5,554,182 A | 9/1996 | Dinh et al. | 5,800,507 A | 9/1998 | Schwartz |
| 5,554,954 A | 9/1996 | Takahashi | 5,800,508 A | 9/1998 | Goicoechea et al. |
| 5,556,413 A | 9/1996 | Lam | 5,807,861 A | 9/1998 | Klein et al. |
| 5,562,922 A | 10/1996 | Lambert | 5,811,447 A | 9/1998 | Kunz et al. |
| 5,563,146 A | 10/1996 | Morris et al. | 5,820,917 A | 10/1998 | Tuch |
| 5,569,197 A | 10/1996 | Helmus et al. | 5,820,918 A | 10/1998 | Ronan et al. |
| 5,569,295 A | 10/1996 | Lam | 5,824,048 A | 10/1998 | Tuch |
| 5,571,166 A | 11/1996 | Dinh et al. | 5,824,049 A | 10/1998 | Ragheb et al. |
| 5,574,059 A | 11/1996 | Regunathan et al. | 5,833,651 A | 11/1998 | Donovan et al. |
| 5,578,075 A | 11/1996 | Dayton | 5,837,008 A | 11/1998 | Berg et al. |
| 5,580,873 A | 12/1996 | Bianco et al. | 5,837,313 A | 11/1998 | Ding et al. |
| 5,580,874 A | 12/1996 | Bianco et al. | 5,843,172 A | 12/1998 | Yan |
| 5,591,140 A | 1/1997 | Narayanan et al. | 5,849,034 A | 12/1998 | Schwartz |
| 5,591,197 A | 1/1997 | Orth et al. | 5,851,217 A | 12/1998 | Wolff et al. |
| 5,591,224 A | 1/1997 | Schwartz et al. | 5,851,231 A | 12/1998 | Wolff et al. |
| 5,591,227 A | 1/1997 | Dinh et al. | 5,858,990 A | 1/1999 | Walsh |
| 5,599,352 A | 2/1997 | Dinh et al. | 5,861,027 A | 1/1999 | Trapp |
| 5,603,722 A | 2/1997 | Phan et al. | 5,865,814 A | 2/1999 | Tuch |
| 5,605,696 A | 2/1997 | Eury et al. | 5,871,535 A | 2/1999 | Wolff et al. |
| 5,607,463 A | 3/1997 | Schwartz et al. | 5,873,904 A | 2/1999 | Ragheb et al. |
| 5,607,475 A | 3/1997 | Cahalan et al. | 5,876,433 A | 3/1999 | Lunn |
| 5,609,629 A | 3/1997 | Fearnot et al. | 5,879,697 A | 3/1999 | Ding et al. |
| 5,620,984 A | 4/1997 | Bianco et al. | 5,882,335 A | 3/1999 | Leone et al. |
| 5,621,102 A | 4/1997 | Bianco et al. | 5,883,651 A | 3/1999 | Thiel et al. .................... 347/71 |
| 5,622,975 A | 4/1997 | Singh et al. | 5,891,108 A | 4/1999 | Leone et al. |
| 5,624,411 A | 4/1997 | Tuch | 5,900,246 A | 5/1999 | Lambert |
| 5,628,785 A | 5/1997 | Schwartz et al. | 5,902,266 A | 5/1999 | Leone et al. |
| 5,629,077 A | 5/1997 | Turnlund et al. | 5,924,997 A | 7/1999 | Campbell ................... 600/549 |
| 5,629,315 A | 5/1997 | Bianco et al. | 5,951,586 A | 9/1999 | Berg et al. |
| 5,632,763 A | 5/1997 | Glastra | 5,957,971 A | 9/1999 | Schwartz |
| 5,632,840 A | 5/1997 | Campbell | 5,972,027 A | 10/1999 | Johnson |
| 5,637,113 A | 6/1997 | Tartaglia et al. | 5,976,534 A | 11/1999 | Hart et al. |
| 5,643,312 A | 7/1997 | Fischell et al. | 5,977,163 A | 11/1999 | Li et al. |
| 5,643,939 A | 7/1997 | Ohlstein | 5,980,553 A | 11/1999 | Gray et al. |
| 5,646,160 A | 7/1997 | Morris et al. | 5,980,566 A | 11/1999 | Alt et al. |
| 5,648,357 A | 7/1997 | Bianco et al. | 5,980,972 A | 11/1999 | Ding |
| 5,649,952 A | 7/1997 | Lam | 5,981,568 A | 11/1999 | Kunz et al. |
| 5,649,977 A | 7/1997 | Campbell | 5,985,307 A | 11/1999 | Hanson et al. |
| 5,651,174 A | 7/1997 | Schwartz et al. | 5,997,468 A | 12/1999 | Wolff et al. |
| 5,652,243 A | 7/1997 | Bianco et al. | 6,004,346 A | 12/1999 | Wolff et al. |
| 5,653,992 A | 8/1997 | Bezwada et al. | 6,039,721 A | 3/2000 | Johnson et al. |
| 5,662,609 A | 9/1997 | Slepian | 6,059,813 A | 5/2000 | Vrba et al. |
| 5,665,728 A | 9/1997 | Morris et al. | 6,071,305 A | 6/2000 | Brown et al. |
| 5,669,924 A | 9/1997 | Shaknovich | 6,074,659 A | 6/2000 | Kunz et al. |
| 5,670,506 A | 9/1997 | Leigh et al. | 6,080,190 A | 6/2000 | Schwartz |
| 5,674,242 A | 10/1997 | Phan et al. | 6,096,070 A | 8/2000 | Ragheb et al. |
| 5,679,400 A | 10/1997 | Tuch | 6,099,562 A | 8/2000 | Ding et al. ................ 623/1.46 |
| 5,679,659 A | 10/1997 | Verhoeven et al. | 6,120,536 A | 9/2000 | Dinge et al. |
| 5,693,085 A | 12/1997 | Buirge et al. | 6,136,798 A | 10/2000 | Cody et al. |
| 5,697,967 A | 12/1997 | Dinh et al. | 6,140,127 A | 10/2000 | Sprague |
| 5,697,971 A | 12/1997 | Fischell et al. | 6,146,358 A | 11/2000 | Rowe |
| 5,700,286 A | 12/1997 | Tartaglia et al. | 6,153,252 A | 11/2000 | Hossainy et al. |
| 5,707,385 A | 1/1998 | Williams | 6,171,232 B1 | 1/2001 | Papandreou et al. |
| 5,709,874 A | 1/1998 | Hanson et al. | 6,171,609 B1 | 1/2001 | Kunz |
| 5,725,549 A | 3/1998 | Lam | 6,177,272 B1 | 1/2001 | Nabel et al. |
| 5,725,567 A | 3/1998 | Wolff et al. | 6,179,817 B1 | 1/2001 | Zhong ....................... 604/265 |
| 5,728,150 A | 3/1998 | McDonald et al. | 6,214,901 B1* | 4/2001 | Chudzik et al. ............ 523/113 |
| 5,728,420 A | 3/1998 | Keogh | 6,240,616 B1 | 6/2001 | Yan |
| 5,731,326 A | 3/1998 | Hart et al. | 6,245,026 B1 | 6/2001 | Campbell et al. ........... 600/549 |
| 5,733,327 A | 3/1998 | Igaki et al. | 6,254,632 B1 | 7/2001 | Wu et al. |
| 5,733,920 A | 3/1998 | Mansuri et al. | 6,254,634 B1 | 7/2001 | Anderson et al. .......... 623/1.42 |
| 5,733,925 A | 3/1998 | Kunz et al. | 6,258,121 B1 | 7/2001 | Yang et al. |
| 5,735,897 A | 4/1998 | Buirge | 6,268,390 B1 | 7/2001 | Kunz |
| 5,739,138 A | 4/1998 | Bianco et al. | 6,273,913 B1 | 8/2001 | Wright et al. |
| 5,755,734 A | 5/1998 | Richter et al. | 6,287,320 B1 | 9/2001 | Slepian |
| 5,769,883 A | 6/1998 | Buscemi et al. | 6,287,628 B1 | 9/2001 | Hossainy et al. |
| 5,776,184 A | 7/1998 | Tuch | 6,299,604 B1 | 10/2001 | Ragheb et al. |
| 5,780,476 A | 7/1998 | Underiner et al. | 6,306,144 B1 | 10/2001 | Sydney et al. .............. 606/108 |
| 5,782,908 A | 7/1998 | Cahalan et al. | 6,306,166 B1 | 10/2001 | Barry et al. |
| 5,788,979 A | 8/1998 | Alt | 6,306,176 B1 | 10/2001 | Whitbourne |

| | | | |
|---|---|---|---|
| 6,306,421 B1 | 10/2001 | Kunz et al. | |
| 6,309,380 B1 | 10/2001 | Larson et al. | |
| 6,309,660 B1 | 10/2001 | Hsu et al. | |
| 6,313,264 B1 | 11/2001 | Caggiano et al. | |
| 6,425,898 B1 | 7/2002 | Wilson et al. | 606/108 |
| 6,713,119 B2* | 3/2004 | Hossainy et al. | 427/2.25 |
| 2001/0007083 A1 | 7/2001 | Roorda | |
| 2001/0029660 A1 | 10/2001 | Johnson | |
| 2001/0032014 A1 | 10/2001 | Yang et al. | |
| 2001/0034363 A1 | 10/2001 | Li et al. | |
| 2001/0037145 A1 | 11/2001 | Guruwaiya et al. | |
| 2002/0026236 A1* | 2/2002 | Helmus et al. | 623/1.42 |
| 2002/0041899 A1 | 4/2002 | Chudzik et al. | 424/487 |
| 2002/0111590 A1 | 8/2002 | Davila et al. | |
| 2003/0077310 A1* | 4/2003 | Pathak et al. | 424/423 |
| 2004/0102758 A1 | 5/2004 | Davila et al. | |

FOREIGN PATENT DOCUMENTS

| | | |
|---|---|---|
| EP | 540290 A2 | 10/1992 |
| EP | 0 586 310 A1 | 4/1993 |
| EP | 0568310 A | 11/1993 |
| EP | 604 022 A1 | 6/1994 |
| EP | 621 015 A1 | 10/1994 |
| EP | 623 354 A1 | 11/1994 |
| EP | 734698 A2 | 3/1996 |
| EP | 0 712 615 | 5/1996 |
| EP | 0 716 836 | 6/1996 |
| EP | 716 836 A1 | 6/1996 |
| EP | 800801 A1 | 8/1996 |
| EP | 734 721 A2 | 10/1996 |
| EP | 0 761 251 | 3/1997 |
| EP | 830853 A1 | 7/1997 |
| EP | 0 850 651 | 7/1998 |
| EP | 0 938 878 A2 | 9/1999 |
| EP | 0 938 878 A3 | 9/1999 |
| EP | 0 950 386 A2 | 10/1999 |
| FR | 0 566 807 A1 | 4/1992 |
| GB | 0 662 307 A2 | 12/1951 |
| GB | 1 205 743 | 9/1970 |
| WO | WO 91/12779 A1 | 9/1991 |
| WO | WO 92/15286 A1 | 9/1992 |
| WO | WO 94/01056 A1 | 1/1994 |
| WO | WO 94/21308 A1 | 9/1994 |
| WO | WO 94/21309 A1 | 9/1994 |
| WO | WO 94/24961 A1 | 11/1994 |
| WO | WO 96/00272 A1 | 1/1996 |
| WO | WO 96/26689 B1 | 9/1996 |
| WO | WO 96/32907 | 10/1996 |
| WO | WO 96/34580 | 11/1996 |
| WO | WO 97/25000 A1 | 7/1997 |
| WO | WO 97/33534 A1 | 9/1997 |
| WO | WO 98/19628 | 5/1998 |
| WO | WO 98/23228 | 6/1998 |
| WO | 98/33443 A1 | 8/1998 |
| WO | WO 98/34669 | 8/1998 |
| WO | WO 98/36784 A1 | 8/1998 |
| WO | WO 98/47447 A1 | 10/1998 |
| WO | WO 98/56312 A1 | 12/1998 |
| WO | WO 00/21584 A | 4/2000 |
| WO | WO 00/27445 A | 5/2000 |
| WO | WO 00/32255 A | 6/2000 |
| WO | WO 01/87342 A2 | 11/2001 |
| WO | WO 02/26139 A1 | 4/2002 |
| WO | WO 02/26281 A1 | 4/2002 |
| WO | WO 03/000308 A1 | 1/2003 |
| WO | WO 03/015664 A1 | 2/2003 |
| WO | WO 03/057218 A1 | 7/2003 |

OTHER PUBLICATIONS

European Search Report, dated Mar. 1, 2004, for European Appln. No. 03 07 8948.

European First Examination Report dated Dec. 2, 2004 for corresponding Appln. No. EP 02 747 953.4.

Ajroldi, G. et al., "Fluoroelastomers-dependence of relaxation phenomena on composition," Polymer, 1989, 30, 2180-2187.

Berk, B. C. et., "Heparins and Glucocorticoids Inhibit Restenosis," J. Am. Coll. Cardiol., 1991, 17, 111B-117B.

Brehm, B. R. et al., "Beta-blockers of the third generation inhibit endothelin-1 liberation, mRNA production and proliferation of human coronary smooth muscle and endothelial cells," J Cardiovasc Pharmacol, Nov. 2000, 36(5 Suppl 1), S401-S403.

Campbell, G. R. and Campbell, J. H., "Phenotypic Modulation of Smooth Muscle Cells in Primary Culture," In: *Vascular Smooth Muscle in Culture*, vol. 1, Ch. 4, Boca Raton, FL: CRC, 1987, pp. 39-55.

Campbell, G. R., et al., "Smooth muscle phenotypic changes in arterial wall homeostasis: implications for the pathogenesis of atherosclerosis," Exp. Mol. Pathol., Apr. 1985, 42(2), 139-162.

Carrera, C. J. et al., "Potent toxicity of 2-chlorodeoxyadenosine toward human monocytes in vitro and in vivo. A novel approach to immunosuppressive therapy," J. Clin, Invest, 1990 86(5), 1480-1488.

Carson, D. A. et al., "DNA strand breaks, NAD metabolism, and programmed cell death," Exp Cell Res, Jun. 1986, 164(2), 273-281.

Carson, D. A. et al., "Genetic analysis of deoxyadenosine toxicity in dividing human lymphoblasts," Adv Exp Med Biol, 1986, 195 Pt B, 207-211.

Carson, D. A. et al., "Lymphocyte dysfunction after DNA damage by toxic oxygen species. A model of immunodeficiency," J Exp Med., Mar. 1, 1986; 163(3), 746-751.

Carson, D. A. et al., "Metabolism to methionine and growth stimulation by 5'-methylthioadenosine and 5'-methylthioinosine in mammalian cells," Biochem Biophys Res Commun, Apr. 29, 1983, 112(2), 391-397.

Carson, D. A. et al., "Specific toxicity of 2-chlorodeoxyadenosine toward resting and proliferating human lymphocytes," Blood, Oct. 1983, 62(4), 737-743.

Chang, M. W. et al., "Adenovirus-mediated Over-expression of the Cyclin/Cyclin-dependent," J. Clin. Invest., 1995, 96, 2260-2268.

Clowes, A. W. et al., "Kinetics of cellular proliferation after arterial injury. II. Inhibition of smooth muscle growth by heparin," Lab. Invest., 1985, 52(6), 611-616.

Clowes, A. W. et al., "Kinetics of cellular proliferation after arterial injury. IV. Heparin inhibits rat smooth muscle mitogenesis and migration," Circ. Res., 1986, 58(6), 839-845.

Clowes, A. W. et al., "Significance of quiescent smooth muscle migration in the injured rat carotid artery," Circ Res. 1985, 56(1), 139-145.

Clowes, A. W., "Suppression by heparin of smooth muscle cell proliferation in injured arteries," Nature, 1977, 265(5595), 625-626.

Colburn, M. D. et al., "Dose responsive suppression of myointimal hyperplasia by dexamethasone," J. Vasc. Surg., 1992, 15, 510-518.

Currier, J. W. et al., "Colchicine Inhibits Restenosis After Iliac Angioplasty in the Atherosclerotic Rabbit," Supplement to Circulation. Abstracts From the 62nd Scientific Sessions., 1989, 80(4), Abstract No. 0263.

Edelman, E. R. et al., "Pathobiologic responses to stenting," Am J. Cardiol. 1998, 81(7A), 4E-6E.

Farb, A. et al., "Vascular smooth muscle cell cytotoxicity and sustained inhibition of neointimal formation by fibroblast growth factor 2-saporin fusion protein," Circ. Res., 1997, 80, 542-550.

Ferns, G. A. A. et al., "Inhibition of Neointimal Smooth Muscle Accumulation After Angioplasty by an Antibody to PDGF," Science, 1991, 253, 1129-1132.

Fischman, D. L. et al., "A Randomized Comparison of Coronary-Stent Placement and Balloon Angioplasty in the Treatment of Coronary Artery Disease," N. Eng. J. Med., Aug. 25, 1994, 331(8), 496-501.

Franklin, S. M. et al., "Pharmacologic prevention of restenosis after coronary angioplasty: review of the randomized clinical trials," Coron Artery Dis. Mar. 1993, 4(3), 232-242.

Fukuyama, J. et al., "Tranilast suppresses the vascular intimal hyperplasia after balloon injury in rabbits fed on a high-cholesterol diet," Eur. J. Pharmacol., 1996, 318, 327-332.

Guyton, J. R. et al., "Inhibition of rat arterial smooth muscle cell proliferation by heparin. In vivo studies with anticoagulant and nonanticoagulant heparin," Circ. Res., 1980, 46, 625-634.

Hanson, S. R. et al., "Interruption of acute platelet-dependent thrombosis by the synthetic antithrombin D-phenylalanyl-L-prolyl-L-arginyl chloromethyl ketone," Proc. Natl. Acad. Sci. USA, 1988, 85, 3184-3188.

Hansson, G. K. et al., "Interferon-γ Inhibits Arterial Stenosis After Injury," Circ., 1991, 84, 1266-1272.

Jonasson, J. et al., "Cyclosporin A inhibits smooth muscle proliferation in the vascular response to injury," Proc. Natl., Acad. Sci., 1988, 85, 2303-2306.

Lang, R. J. et al., "Effects of 2,3-butanedione monoxime on whole-cell Ca2+ channel currents in single cells of the guinea-pig taenia caeci," J Physiol. Feb. 1991, 433, 1-24.

Lang, R. J. et al., "Effects of okadaic acid and ATP gamma S on cell length and Ca(2+)-channel currents recorded in single smooth muscle cells of the guinea-pig taenia caeci., ", Br. J. Pharmacol., Oct. 1991, 104(2), 331-336.

Liu, M. W. et al., "Trapidil in Preventing Restenosis After Balloon Angioplasty in the Atherosclerotic Rabbit," Circ., 1990, 81, 1089-1093.

Lundergan, C. F. et al., "Peptide Inhibition of Myointimal Proliferation by Agiopeptin, a Somatostatin Analogue," JACC., 1991, 17(6), 132B-136B.

Majesky, M. W. et al., "Heparin regulates smooth muscle S phase entry in the injured rat carotid artery," Circ. Res., 1987, 61, 296-300.

Mak, K-H. et al., "Clinical trials to prevent restenosis after percutaneous coronary revascularization," Ann N Y Acad Sci., Apr. 15, 1997, 811, 255-84; discussion 284-8. Review.

Marx, S. O. et al., "Rapamycin-FKBP Inhibits Cell Cycle Regulators of Proliferation in Vascular Smooth Muscle Cells," Circ. Res., 1995, 76, 412-417.

Mintz, G. S. et al., "Arterial remodeling after coronary angioplasty: a serial intravascular ultrasound study," Circulation. Jul. 1, 1996, 94(1), 35-43.

Mintz, G. S. et al., "Axial plaque redistribution as a mechanism of percutaneous transluminal coronary angioplasty," Am J Cardiol, Feb. 15, 1996, 77(5), 427-430.

Mintz, G. S. et al., "Intravascular Ultrasound Assessment of the Mechanisms and Predictors of Restenosis Following Coronary Angioplasty," J Invasive Cardiol., Jan. 1996, 8(1), 1-14.

Mintz, G. S. et al., "Intravascular ultrasound findings after excimer laser coronary angioplasty," Cathet Cardiovasc Diagn. Feb. 1996, 37(2), 113-118.

Mintz, G. S. et al., "Intravascular ultrasound predictors of restenosis after percutaneous transcatheter coronary revascularization," J Am Coll Cardiol, Jun. 1996, 27(7), 1678-1687.

Mintz, G. S. et al., "Intravascular ultrasound to discern device-specific effects and mechanisms of restenosis," Am J Cardiol. Aug. 14, 1996, 78(3A), 18-22.

Mintz, G. S. et al., "Limitations of angiography in the assessment of plaque distribution in coronary artery disease: a systematic study of target lesion eccentricity in 1446 lesions," Circulation. Mar. 1, 1996, 93(5), 924-931.

*Modern Fluoropolymers*, (J. Scheirs, ed.), John Wiley & Sons, New York, 1997, pp. 77-87.

Nemecek, G. M. et al., "Terbinafine Inhibits the Mitogenic Response to Platelet-Derived Growth Factor *in Vitro* and Neoinimal Proliferation *in Vivo*, " J. Pharmacol. Exp. Thera., 1989, 248, 1167-1174.

Okada, T. et al., "Localized Release of Perivascular Heparin Inhibits Intimal Proliferation after Endothelial Injury without Systematic Anticoagulation," Neurosurgery, 1989, 25, 892-898.

Popma, J. J. et al., "Atherectomy of right coronary ostial stenoses: initial and long-term results, technical features and histologic findings," Am J Cardiol., Feb. 15,1991; 67(5), 431-433.

Popma, J. J. et al., "Adjuncts to thrombolysis for myocardial reperfusion," Ann Intern Med., Jul. 1, 1991, 115(1), 34-44.

Popma, J. J. et al., "Clinical trials of restenosis after coronary angioplasty," Circulation, Sep. 1991, 84(3), 1426-1436.

Popma, J. J. et al. "Clinical, angiographic and procedural correlates of quantitative coronary dimensions after directional coronary atherectomy," J Am Coll Cardiol., Nov. 1, 1991, 18(5), 1183-1189.

Powell, J. S. et al., "Inhibitors of Angiotensin-Converting Enzyme Prevent Myointimal Proliferation After Vascular Injury," Science, 1989, 245, 186-188.

Serruys, P. W. et al., "A comparison of balloon-expandable-stent implantation with balloon angiplasty in patients with coronary artery disease," N Engl J Med, Aug. 25, 1994; 331(8), 489-495.

Serruys, P. W. et al., "Evaluation of ketanserin in the prevention of restenosis after percutaneous transluminal coronary angioplasty. A multicenter randomized double-blind placebo-controlled trial," Circulation. Oct.1993; 88(4 Pt 1), 1588-1601.

Serruys, P. W. et al., "Heparin-coated Palmaz-Schatz stents in human coronary arteries. Early outcome of the Benestent-II Pilot Study," Circulation, Feb 1, 1996; 93(3), 412-422.

Serruys, P. W. et al., "Randomized trials of coronary stenting," J Interv Cardiol, Aug. 1994; 7(4), 331.

Serruys, P. W. et al., "Restenosis revisited: insights provided by quantitative coronary angiography," Am Heart J, Nov. 1993; 126(5), 1243-1267.

Serruys, P. W. et al., "The bailout stent. Is a friend in need always a friend indeed?" Circulation, Nov. 1993; 88(5 Pt 1), 2455-2457.

Seto, S. et al., "Mechanism of deoxyadenosine and 2-chlorodeoxyadenosine toxicity to nondividing human lymphocytes," J Clin Invest, Feb. 1985, 75(2), 377-383.

Simons, M. et al., "Antisense c-*myb* oliggonucleotides inhibit intimal arterial smooth muscle cell accumulation in *vivo*," Nature, 1992, 359, 67-70.

Snow, A. D. et al., "Heparin modulates the composition of the extracellular matrix domain surrounding arterial smooth muscle cells," Am. J. Pathol., 1990, 137, 313-330.

Sollot, S. J. et al., "Taxol Inhibits Neointimal Smooth Muscle Cell Accumulation after Angioplasty in the Rat," J. Clin. Invest., 1995, 95, 1869-1876.

Tanaka, H. et al., "Sustained activation of vascular cells and leukocytes in the rabbit aorta after balloon injury," Circulation, Oct. 1993; 88(4 Pt 1), 1788-1803.

Tardif, et al., "Probucol and multivitamins in the prevention of restenosis after coronary angioplasty. Multivitamins and Probucol Study Group," N Engl J Med. Aug. 7, 1997; 337(6), 365-372.

Teirstein, P. S. et al., "Catheter-based radiotherapy to inhibit restenosis after coronary stenting," N Engl J Med., Jun. 12, 1997; 336(24), 1697-1703.

Weinberger, J. et al., "Intracoronary irradiation: dose response for the prevention of restenosis in swine," Int. J. Rad. Onc. Biol. Phys., 1996, 36, 767-775.

Yokoi, H. et al., "Effectiveness of an antioxidant in preventing restenosis after percutaneous transluminal coronary angioplasty: the Probucol Angioplasty Restenosis Trial," J Am Coll Cardiol., Oct. 1997; 30(4), 855-862.

\* cited by examiner

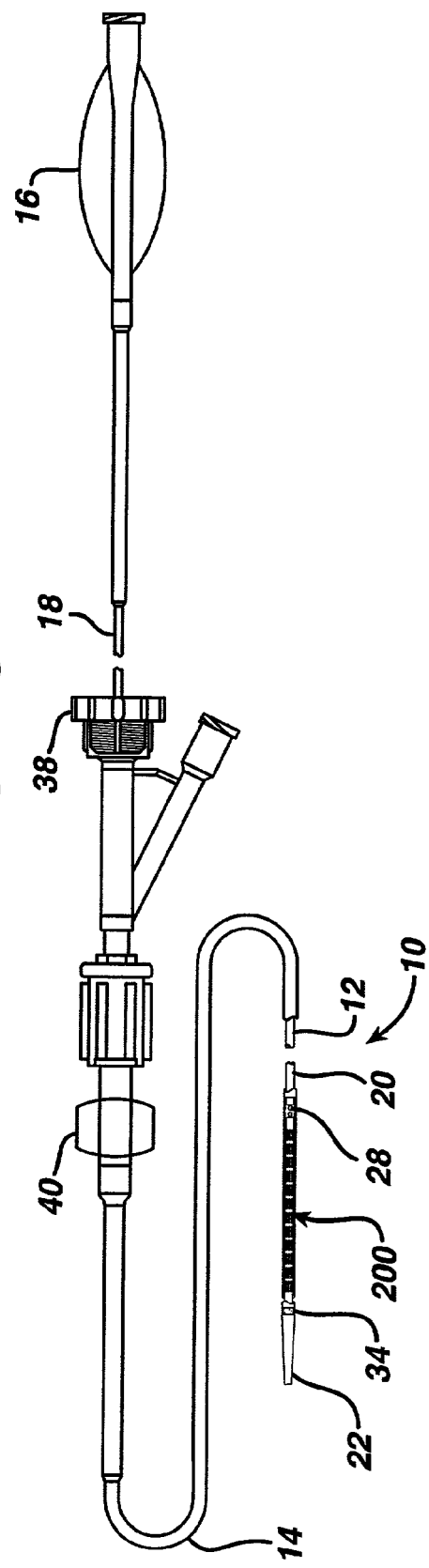
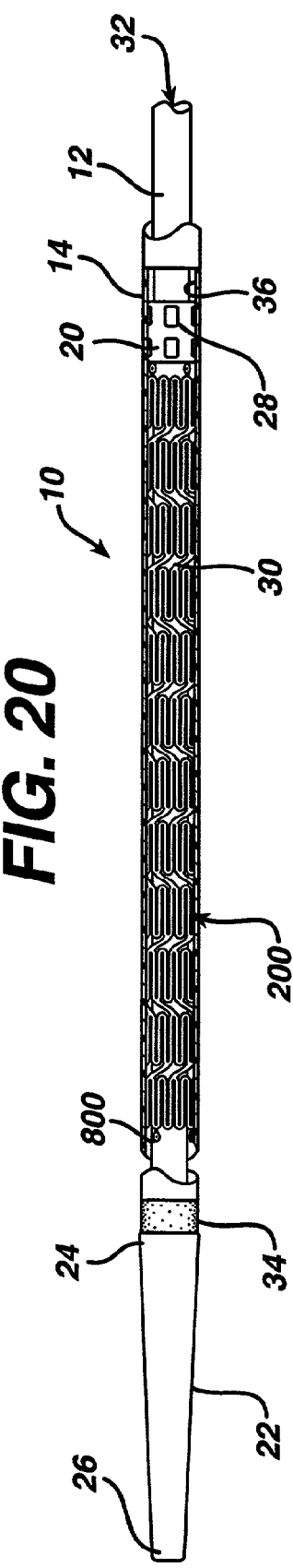

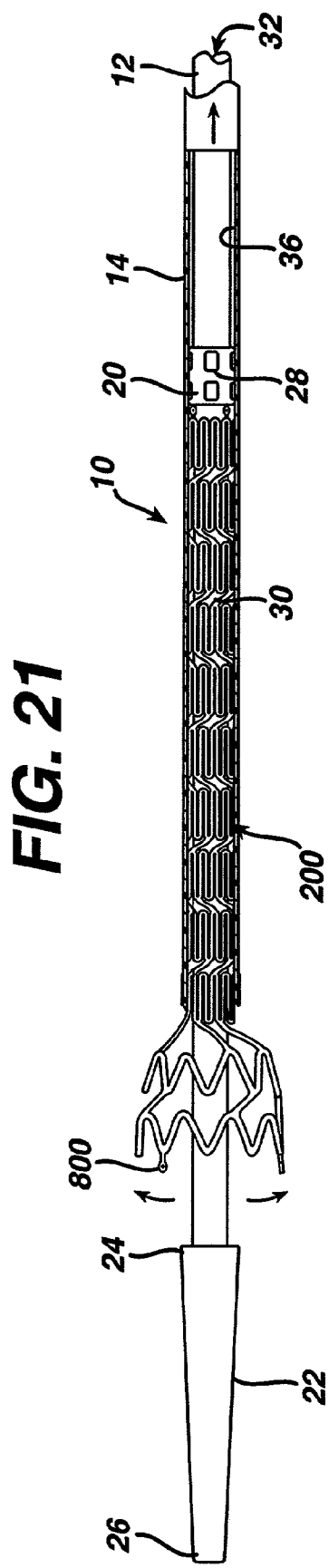

COATED MEDICAL DEVICES FOR THE TREATMENT OF VULNERABLE PLAQUE

CROSS REFERENCE TO RELATED APPLICATIONS

This application is a continuation-in-part application of U.S. application Ser. No. 09/962,496 filed Sep. 25, 2001 now abandoned.

BACKGROUND OF THE INVENTION

1. Field of the Invention

The present invention relates to the local administration of drug/drug combinations for the prevention and treatment of vascular disease, and more particularly to intraluminal medical devices for the local delivery of drug/drug combinations for the prevention and treatment of vascular disease caused by injury and methods for maintaining the drug/drug combinations on the intraluminal medical devices. The present invention also relates to medical devices having drugs, agents or compounds affixed thereto to minimize or substantially eliminate a biological organism's reaction to the introduction of the medical device to the organism. The present invention also relates to medical devices having drugs, agents or compounds affixed thereto for treating vulnerable plaque.

2. Discussion of the Related Art

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure, and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed anti-proliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25–26, 1977; Guyton, J. R. et al., Circ. Res., 46: 625–634, 1980; Clowes, A. W. and Clowes, M. M., Lab. Invest. 52: 611–616, 1985; Clowes, A. W. and Clowes, M. M., Circ. Res. 58: 839–845, 1986; Majesky et al., Circ. Res. 61: 296–300, 1987; Snow et al., Am. J. Pathol. 137: 313–330, 1990; Okada, T. et al., Neurosurgery 25: 92–98, 1989), colchicine (Currier, J. W. et al., Circ. 80: 11–66, 1989), taxol (Sollot, S. J. et al., J. Clin. Invest. 95: 1869–1876, 1995), angiotensin converting enzyme (ACE) inhibitors (Powell, J. S. et al., Science, 245: 186–188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129–1132, 1991), terbinafine (Nemecek, G. M. et al., J. Pharmacol. Exp. Thera. 248: 1167–1174, 1989), trapidil (Liu, M. W. et al., Circ. 81: 1089–1093, 1990), tranilast (Fukuyama, J. et al., Eur. J. Pharmacol. 318: 327–332, 1996), interferon-gamma (Hansson, G. K. and Holm, J., Circ. 84: 1266–1272, 1991), rapamycin (Marx, S. O. et al., Circ. Res. 76: 412–417, 1995), steroids (Colburn, M. D. et al., J. Vasc. Surg. 15: 510–518, 1992), see also Berk, B. C. et al., J. Am. Coll. Cardiol. 17: 111B-117B, 1991), ionizing radiation (Weinberger, J. et al., Int. J. Rad. Onc. Biol. Phys. 36: 767–775, 1996), fusion toxins (Farb, A. et al., Circ. Res. 80: 542–550, 1997) antisense oligionucleotides (Simons, M. et al., Nature 359: 67–70, 1992) and gene vectors (Chang, M. W. et al., J. Clin. Invest. 96: 2260–2268, 1995). Antiproliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute re-occlusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent postangioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is through diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/ therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

One class of biostable materials that has been reported as coatings for stents is polyfluoro homopolymers. Polytetrafluoroethylene (PTFE) homopolymers have been used as implants for many years. These homopolymers are not soluble in any solvent at reasonable temperatures and therefore are difficult to coat onto small medical devices while maintaining important features of the devices (e.g. slots in stents).

Stents with coatings made from polyvinylidenefluoride homopolymers and containing pharmaceutical/therapeutic agents or drugs for release have been suggested. However, like most crystalline polyfluoro homopolymers, they are difficult to apply as high quality films onto surfaces without subjecting them to relatively high temperatures, that correspond to the melting temperature of the polymer.

It would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices even when such coated devices are subjected to relatively low maximum temperatures.

Another type of vascular disease of considerable concern is atherosclerosis. Atherosclerosis is a thickening and hardening of the arteries and is generally believed to be caused by the progressive buildup of fatty substances, e.g. cholesterol, inflammatory cells, cellular waste products, calcium and other substances in the inner lining or intima of the arteries. The buildup of these irritating substances may in turn stimulate cells in the walls of the affected arteries to produce additional substances that result in the further buildup of cells leading to the growth of a lesion. This buildup or lesion is generally referred to as plaque.

Recent studies have lead to a shift in the understanding of atherosclerosis and uncovered another major vascular problem not yet well treated. Scientists theorize that at least some coronary disease is an inflammatory process, in which inflammation causes plaque to destabilize and rupture. This inflamed plaque is known as atherosclerotic vulnerable plaque.

Vulnerable plaque consists of a lipid-rich core covered by a thin layer of smooth muscle cells. These vulnerable plaques are prone to rupture and erosion, and can cause significant infarcts if the thin cellular layer ruptures or ulcerates. When the inflammatory cells erode or rupture, the lipid core is exposed to the blood flow, forming thrombi in the artery. These thrombi may grow rapidly and block the artery, or detach and travel downstream, leading to embolic events, unstable angina, myocardial infarction, and/or sudden death. In fact, some recent studies have suggested that plaque rupture may trigger sixty to seventy percent of all fatal myocardial infarctions. See U.S. Pat. No. 5,924,997 issued to Campbell and U.S. Pat. No. 6,245,026 issued to Campbell et al. for further descriptions of vulnerable plaques.

Early methods used to detect atherosclerosis lacked the diagnostic tools to visualize and identify vulnerable plaque in cardiac patients. However, new diagnostic technologies are under development to identify the location of vulnerable plaques in the coronary arteries. These new devices include refined magnetic resonance imaging (MRI), thermal sensors that measure the temperature of the arterial wall on the premise that the inflammatory process generates heat, elasticity sensors, intravascular ultrasound, optical coherence tomography (OCT), contrast agents, and near-infrared and infrared light. What is not currently clear, however, is how to treat these vulnerable plaque lesions once they are found.

Treating vulnerable plaque by using balloon angioplasty followed by traditional stenting would provide less than satisfactory results. Balloon angioplasty by itself may rupture the vulnerable plaque exposing the underlying fresh tissue cells, collagen or damaged endothelium, to the blood flow. This condition ultimately leads to the formation of a thrombi or blood clot that may partially or completely occlude the vessel. In addition, while bare or uncoated stents will induce neointimal hyperplasia that will provide a protective cover over the vulnerable plaque, restenosis remains a major problem that may create more risk to the patient than the original vulnerable plaque.

Accordingly, it would be advantageous to develop a drug eluting stent or other medical device that effectively treats vulnerable plaque and related vascular disease.

SUMMARY OF THE INVENTION

The medical devices in combination with therapeutic dosages one or more drugs, agents, and/or compounds of the present invention provide a means for overcoming the difficulties associated with the methods and devices currently in use for the treatment of vulnerable plaque and other related vascular disease, as briefly described above.

In accordance with one aspect, the present invention is directed to a medical device for the treatment of vascular disease. The medical device comprises a scaffold structure for maintaining luminal patency, a biocompatible vehicle affixed to at least a portion of the scaffold structure, and one or more agents in therapeutic dosages incorporated into the biocompatible vehicle, wherein the biocompatible vehicle is configured to release the one or more agents over one or more time periods to treat both an acute phase and a chronic phase of the vascular disease.

In accordance with another aspect, the present invention is directed to a medical device for the treatment of atherosclerotic vulnerable plaque. The medical device comprises a stent for maintaining vessel patentcy and providing structural support for a fibrous cap of the vulnerable plaque lesion, a biocompatible vehicle affixed to at least a portion of the stent, at least one first agent in a therapeutic dosage incorporated into the biocompatible vehicle for treating the fibrous cap of the vulnerable plaque lesion, and at least one second agent in a therapeutic dosage incorporated into the biocompatible vehicle for treating a lipid core of the vulnerable plaque lesion, the biocompatible vehicle being configured to release the at least one first agent faster than the at least one second agent and to release the at least one first agent for a shorter duration than the at least one second agent.

In accordance with yet another aspect, the present invention is directed to a method for treating atherosclerotic vulnerable plaque. The method comprises maintaining vessel patentcy and providing structural support for a fibrous cap of the vulnerable plaque lesion through the introduction of a coated stent, releasing at least one first agent in a therapeutic dosage incorporated into the coated stent at a first rate and for a first duration for treating the fibrous cap of the vulnerable plaque lesion, and releasing at least one second agent in a therapeutic dosage incorporated into the coated stent at a second rate and for a second duration for treating a lipid core of the vulnerable plaque lesion, the coated stent being configured to release the at least one first agent faster than the at least one second agent and to release the at least one first agent for a shorter duration than the at least one second agent.

The medical devices, drug coatings and methods for maintaining the drug coatings or vehicles thereon of the present invention utilizes a combination of materials to treat disease, and reactions by living organisms due to the implantation of medical devices for the treatment of disease or other conditions. The local delivery of drugs, agents or compounds generally substantially reduces the potential toxicity of the drugs, agents or compounds when compared to systemic delivery while increasing their efficacy.

Drugs, agents or compounds may be affixed to any number of medical devices to treat various diseases. The drugs, agents or compounds may also be affixed to minimize or substantially eliminate the biological organism's reaction to the introduction of the medical device utilized to treat a separate condition. For example, stents may be introduced to open coronary arteries or other body lumens such as biliary ducts. The introduction of these stents cause a smooth muscle cell proliferation effect as well as inflammation. Accordingly, the stents may be coated with drugs, agents or compounds to combat these reactions.

The drugs, agents or compounds will vary depending upon the type of medical device, the reaction to the introduction of the medical device and/or the disease sought to be treated. The type of coating or vehicle utilized to immobilize the drugs, agents or compounds to the medical device may also vary depending on a number of factors, including the type of medical device, the type of drug, agent or compound and the rate of release thereof.

Vulnerable plaque is a vascular disease wherein a lipid-rich core is covered by a thin layer of smooth muscle cells. These vulnerable plaques are prone to rupture and erosion, and can cause significant infarcts if the thin inflammatory cell layer ruptures or ulcerates. When the inflammatory cells erode or rupture, the lipid core is exposed to the blood flow, forming thrombi in the artery. These thrombi may grow rapidly and block the artery, or detach and travel downstream, leading to embolic events, unstable angina, myocardial infarction, and/or sudden death. The present invention is directed to a scaffold structure designed to maintain vessel patency and which comprises a polymeric coating architecture including one or more therapeutic drugs, agents and/or compounds for treating the inflammation associated with vulnerable plaque rupture and lipid core metabolism. Essentially, the present invention utilizes a dual release rate profile to treat both aspects of vulnerable plaque. Antiinflammatory therapeutic drugs, agents and/or compounds may be incorporated into the coating architecture for fast release to address the inflammatory acute phase of the disease and lipid lowering drugs, agents and/or compounds may be incorporated into the coating architecture for slow release to address the chronic phase of the disease.

In order to be effective, the drugs, agents or compounds should preferably remain on the medical devices during delivery and implantation. Accordingly, various coating techniques for creating strong bonds between the drugs, agents or compounds may be utilized. In addition, various materials may be utilized as surface modifications to prevent the drugs, agents or compounds from coming off prematurely.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 19 is a simplified partial cross-sectional view of a stent delivery apparatus having a stent loaded therein, which can be used with a stent made in accordance with the present invention.

FIG. 20 is a view similar to that of FIG. 19 but showing an enlarged view of the distal end of the apparatus.

FIG. 21 is a perspective view of an end of the stent with the markers in a partially expanded form as it emerges from the delivery apparatus in accordance with the present invention.

DETAILED DESCRIPTION OF THE PREFERRED EMBODIMENTS

Figure 1:
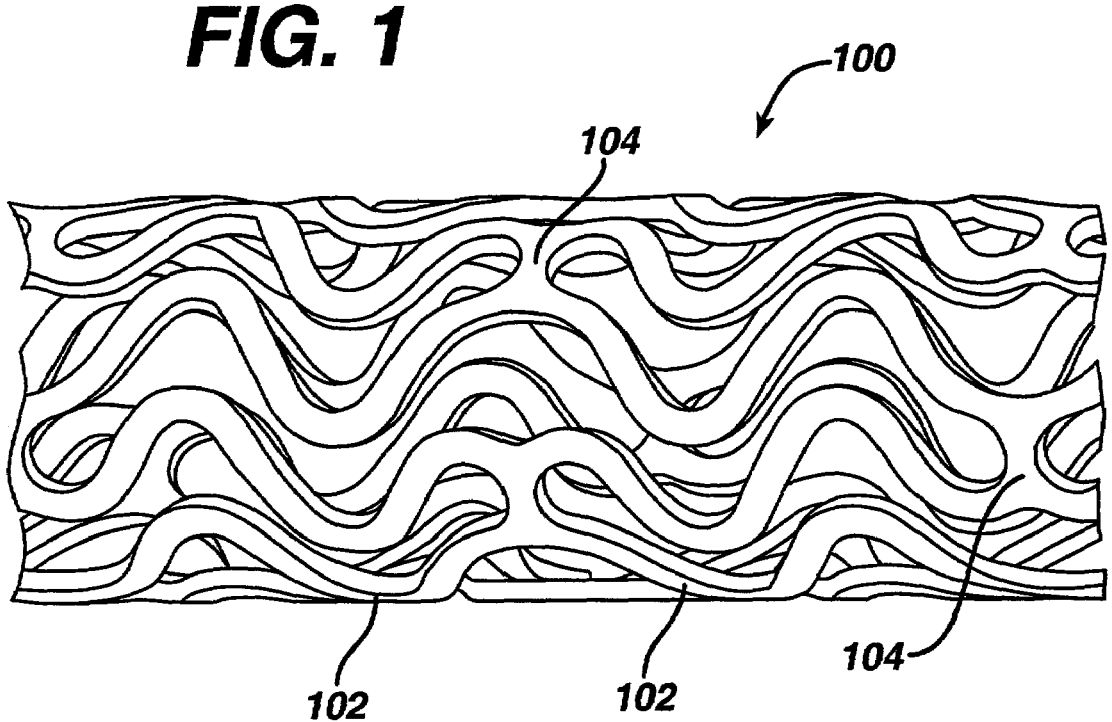
FIG. 1 is a view along the length of a stent (ends not shown) prior to expansion showing the exterior surface of the stent and the characteristic banding pattern.

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach.

Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as $G(GP)II_b III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

FIG. 1 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally-protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one exemplary embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
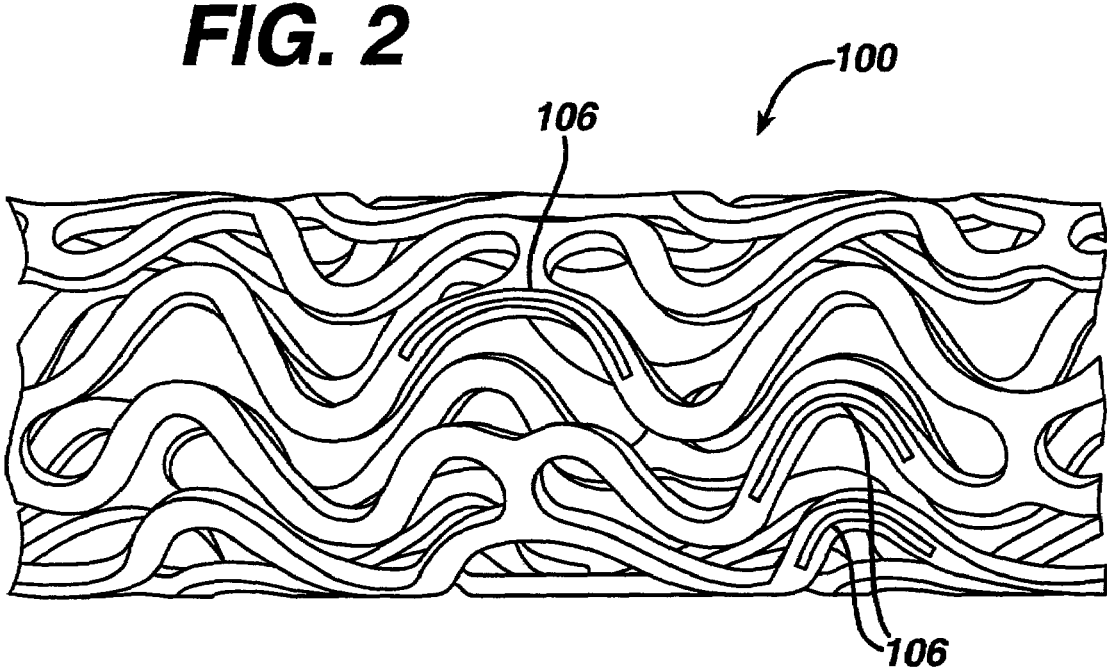
FIG. 2 is a view along the length of the stent of FIG. 1 having reservoirs in accordance with the present invention.

FIG. 2 illustrates an exemplary embodiment of the present invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Figure 26:
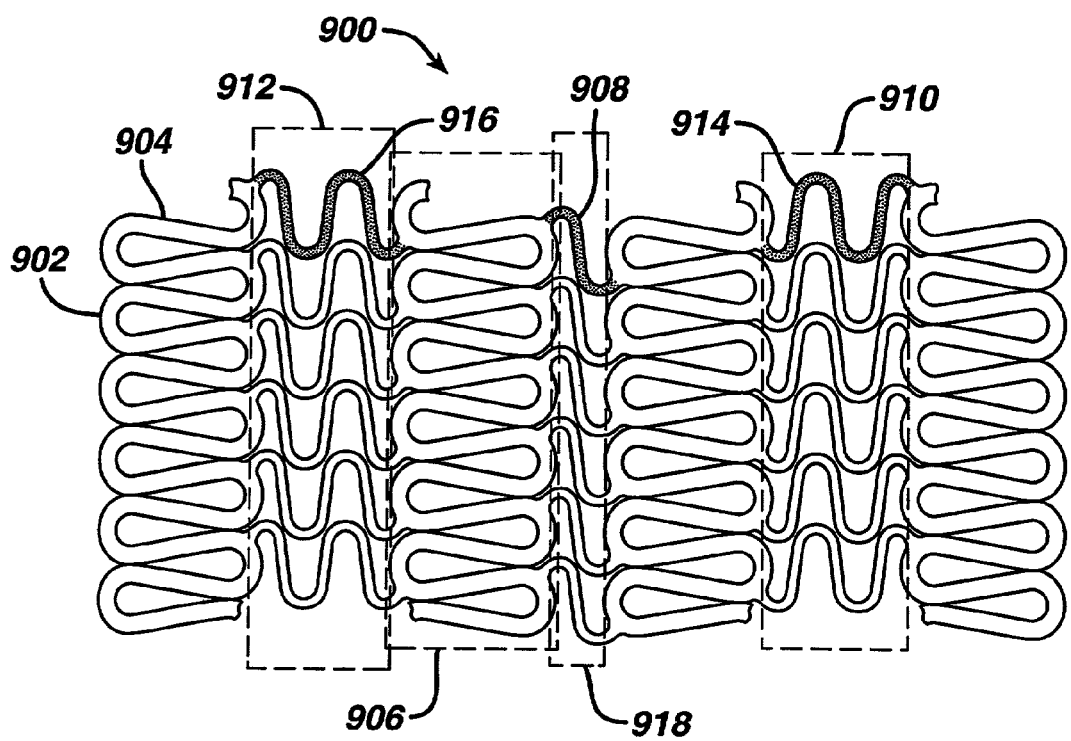
FIG. 26 illustrates an exemplary balloon-expandable stent having an alternative arrangement of "N" and "J" links between sets of strut members, represented on a flat, two-dimensional plan view in accordance with the present invention.

FIG. 26 illustrates another exemplary embodiment of a balloon-expandable stent. FIG. 26 illustrates the stent 900 in its crimped, pre-deployed state as it would appear if it were cut longitudinally and then laid out into a flat, two-dimensional configuration. The stent 900 has curved end struts 902 and diagonal struts 904 with each set of strut members 906 connected by sets of flexible links 908, 910 or 912. In this exemplary embodiment, three different types of flexible links are used. A set of "N" links 910 comprising six circumferentially spaced "N" links 914 and a set of inverted "N" links 912 comprising six circumferentially spaced inverted "N" links 916 each connect to adjacent sets of strut members 906 at the ends of the stent 900. A set of inverted "J" links 918 comprising six circumferentially spaced inverted "J" links 908 are used to connect the adjacent sets of strut members 906 in the center of the stent 900. The shape of the "N" links 914 and inverted "N" links 916 facilitate the links' ability to lengthen and shorten as the stent bends around a curve during delivery into the human body. This ability to lengthen and shorten helps to prevent the sets of strut members from being pushed or pulled off the balloon during delivery into the body and is particularly applicable to short stents which tend to have relatively poor stent retention onto an inflatable balloon. The stent 900 with its greater strength at its central region would advantageously be used for comparatively short stenoses that have a tough, calcified central section. It should also be understood that a regular "J" link could be used for the stent 900 in place of the inverted "J" link 908. Other exemplary embodiments of balloon expandable stents may be found in U.S. Pat. No. 6,190,403 B1 issued on Feb. 20, 2001 and which is incorporated by reference herein.

Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

As used herein, rapamycin includes rapamycin and all analogs, derivatives and congeners that bind to FKBP12, and other immunophilins, and possesses the same pharmacologic properties as rapamycin including inhibition of mTOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycin may be incorporated onto or affixed to the stent in a number of ways. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Any number of non-erodible polymers may be utilized in conjunction with the rapamycin. In one exemplary embodiment, the polymeric matrix comprises two layers. The base layer comprises a solution of poly(ethylene-co-vinylacetate) and polybutylmethacrylate. The rapamycin is incorporated into this base layer. The outer layer comprises only polybutylmethacrylate and acts as a diffusion barrier to prevent the rapamycin from eluting too quickly. The thickness of the outer layer or top coat determines the rate at which the rapamycin elutes from the matrix. Essentially, the rapamycin elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described below.

The poly(ethylene-co-vinylacetate), polybutylmethacrylate and rapamycin solution may be incorporated into or onto the stent in a number of ways. For example, the solution may be sprayed onto the stent or the stent may be dipped into the solution. Other methods include spin coating and RF-plasma polymerization. In one exemplary embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more precise control over the thickness of the coat may be achieved.

In another exemplary embodiment, the rapamycin or other therapeutic agent may be incorporated into a film-forming polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

The present invention provides polymeric coatings comprising a polyfluoro copolymer and implantable medical devices, for example, stents coated with a film of the polymeric coating in amounts effective to reduce thrombosis and/or restenosis when such stents are used in, for example, angioplasty procedures. As used herein, polyfluoro copolymers means those copolymers comprising an amount of a first moiety selected from the group consisting of polymerized vinylidenefluoride and polymerized tetrafluoroethylene, and an amount of a second moiety other than the first moiety and which is copolymerized with the first moiety to produce the polyfluoro copolymer, the second moiety being capable of providing toughness or elastomeric properties to the polyfluoro copolymer, wherein the relative amounts of the first moiety and the second moiety are effective to provide coatings and film made from such polyfluoro copolymers with properties effective for use in coating implantable medical devices.

The coatings may comprise pharmaceutical or therapeutic agents for reducing restenosis, inflammation and/or thrombosis, and stents coated with such coatings may provide sustained release of the agents. Films prepared from certain polyfluoro copolymer coatings of the present invention provide the physical and mechanical properties required of conventional coated medical devices, even where maximum temperature, to which the device coatings and films are exposed, are limited to relatively low temperatures. This is particularly important when using the coating/film to deliver pharmaceutical/therapeutic agents or drugs that are heat sensitive, or when applying the coating onto temperature-sensitive devices such as catheters. When maximum exposure temperature is not an issue, for example, where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g., Modern Fluoropolymers, (J. Shires ed.) John Wiley & Sons, New York, 1997, pp. 77–87.

The present invention comprises polyfluoro copolymers that provide improved biocompatible coatings or vehicles for medical devices. These coatings provide inert biocompatible surfaces to be in contact with body tissue of a mammal, for example, a human, sufficient to reduce restenosis, or thrombosis, or other undesirable reactions. While many reported coatings made from polyfluoro homopolymers are insoluble and/or require high heat, for example, greater than about one hundred twenty-five degrees centigrade, to obtain films with adequate physical and mechanical properties for use on implantable devices, for example, stents, or are not particularly tough or elastomeric, films prepared from the polyfluoro copolymers of the present invention provide adequate adhesion, toughness or elasticity, and resistance to cracking when formed on medical devices. In certain exemplary embodiments, this is the case even where the devices are subjected to relatively low maximum temperatures.

The polyfluoro copolymers used for coatings according to the present invention are preferably film-forming polymers that have molecular weight high enough so as not to be waxy or tacky. The polymers and films formed therefrom should preferably adhere to the stent and not be readily deformable after deposition on the stent as to be able to be displaced by hemodynamic stresses. The polymer molecular weight should preferably be high enough to provide sufficient toughness so that films comprising the polymers will not be rubbed off during handling or deployment of the stent. In certain exemplary embodiments the coating will not crack where expansion of the stent or other medical devices occurs.

Coatings of the present invention comprise polyfluoro copolymers, as defined hereinabove. The second moiety polymerized with the first moiety to prepare the polyfluoro copolymer may be selected from those polymerized, biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

Polyfluoro copolymers used in the present invention typically comprise vinylidinefluoride copolymerized with hexafluoropropylene, in the weight ratio in the range of from about fifty to about ninety-two weight percent vinylidinefluoride to about fifty to about eight weight percent HFP. Preferably, polyfluoro copolymers used in the present invention comprise from about fifty to about eighty-five weight percent vinylidinefluoride copolymerized with from about fifty to about fifteen weight percent HFP. More preferably, the polyfluoro copolymers will comprise from about fifty-five to about seventy weight percent vinylidineflyoride copolymerized with from about forty-five to about thirty weight percent HFP. Even more preferably, polyfluoro copolymers comprise from about fifty-five to about sixty-five weight percent vinylidinefluoride copolymerized with from about forty-five to about thirty-five weight percent HFP. Such polyfluoro copolymers are soluble, in varying degrees, in solvents such as dimethylacetamide (DMAc), tetrahydrofuran, dimethyl formamide, dimethyl sulfoxide and n-methyl pyrrolidone. Some are soluble in methylethylketone (MEK), acetone, methanol and other solvents commonly used in applying coatings to conventional implantable medical devices.

Conventional polyfluoro homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about a maximum predetermined temperature. This is particularly important when the coatings/films comprise pharmaceutical or therapeutic agents or drugs that are heat sensitive, for example, subject to chemical or physical degradation or other heat-induced negative affects, or when coating heat sensitive substrates of medical devices, for example, subject to heat-induced compositional or structural degradation.

Depending on the particular device upon which the coatings and films of the present invention are to be applied and the particular use/result required of the device, polyfluoro copolymers used to prepare such devices may be crystalline, semi-crystalline or amorphous.

Where devices have no restrictions or limitations with respect to exposure of same to elevated temperatures, crystalline polyfluoro copolymers may be employed. Crystalline polyfluoro copolymers tend to resist the tendency to flow under applied stress or gravity when exposed to temperatures above their glass transition (Tg) temperatures. Crystalline polyfluoro copolymers provide tougher coatings and films than their fully amorphous counterparts. In addition, crystalline polymers are more lubricious and more easily handled through crimping and transfer processes used to mount self-expanding stents, for example, nitinol stents.

Semi-crystalline and amorphous polyfluoro copolymers are advantageous where exposure to elevated temperatures is an issue, for example, where heat-sensitive pharmaceutical or therapeutic agents are incorporated into the coatings and films, or where device design, structure and/or use preclude exposure to such elevated temperatures. Semicrystalline polyfluoro copolymer elastomers comprising relatively high levels, for example, from about thirty to about forty-five weight percent of the second moiety, for example, HFP, copolymerized with the first moiety, for example, VDF, have the advantage of reduced coefficient of friction and self-blocking relative to amorphous polyfluoro copolymer elastomers. Such characteristics may be of significant value when processing, packaging and delivering medical devices coated with such polyfluoro copolymers. In addition, such polyfluoro copolymer elastomers comprising such relatively high content of the second moiety serves to control the solubility of certain agents, for example, rapamycin, in the polymer and therefore controls permeability of the agent through the matrix.

Polyfluoro copolymers utilized in the present inventions may be prepared by various known polymerization methods. For example, high pressure, free-radical, semi-continuous emulsion polymerization techniques such as those disclosed in Fluoroelastomers-dependence of relaxation phenomena on compositions, POLYMER 30, 2180, 1989, by Ajroldi, et al., may be employed to prepare amorphous polyfluoro copolymers, some of which may be elastomers. In addition, free-radical batch emulsion polymerization techniques disclosed herein may be used to obtain polymers that are semi-crystalline, even where relatively high levels of the second moiety are included.

As described above, stents may comprise a wide variety of materials and a wide variety of geometrics. Stents may be made of biocomtible materials, including biostable and bioabsorbable materials. Suitable biocompatible metals include, but are not limited to, stainless steel, tantalum, titanium alloys (including nitinol), and cobalt alloys (including cobalt-chromium nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, caprolactone, and blends thereof).

The film-forming biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about fifteen weight percent of the coating, preferably from about 0.4 to about ten weight percent. The polyfluoro copolymer coatings may be applied in one or more coating steps, depending on the amount of polyfluoro copolymer to be applied. Different polyfluoro copolymers may be used for different layers in the stent coating. In fact, in certain exemplary embodiments, it is highly advantageous to use a diluted first coating solution comprising a polyfluoro copolymer as a primer to promote adhesion of a subsequent polyfluoro copolymer coating layer that may include pharmaceutically active materials. The individual coatings may be prepared from different polyfluoro copolymers.

Additionally, a top coating may be applied to delay release of the pharmaceutical agent, or they could be used as the matrix for the delivery of a different pharmaceutically active material. Layering of coatings may be used to stage release of the drug or to control release of different agents placed in different layers.

Blends of polyfluoro copolymers may also be used to control the release rate of different agents or to provide a desirable balance of coating properties, i.e. elasticity, toughness, etc., and drug delivery characteristics, for example, release profile. Polyfluoro copolymers with different solubilities in solvents may be used to build up different polymer layers that may be used to deliver different drugs or to control the release profile of a drug. For example, polyfluoro copolymers comprising 85.5/14.5 (wt/wt) of poly(vinylidinefluoride/HFP) and 60.6/39.4 (wt/wt) of poly(vinylidinefluoride/HFP) are both soluble in DMAc. However, only the 60.6/39.4 PVDF polyfluoro copolymer is soluble in methanol. So, a first layer of the 85.5/14.5 PVDF polyfluoro copolymer comprising a drug could be over coated with a topcoat of the 60.6/39.4 PVDF polyfluoro copolymer made with the methanol solvent. The top coating may be used to delay the drug delivery of the drug contained in the first layer. Alternately, the second layer could comprise a different drug to provide for sequential drug delivery. Multiple layers of different drugs could be provided by alternating layers of first one polyfluoro copolymer, then the other. As will be readily appreciated by those skilled in the art, numerous layering approaches may be used to provide the desired drug delivery.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, for example, nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts may be determined by monitoring the in vitro and/or in vivo release profiles for the therapeutic agents.

The best conditions for the coating application are when the polyfluoro copolymer and pharmaceutic agent have a common solvent. This provides a wet coating that is a true solution. Less desirable, yet still usable, are coatings that contain the pharmaceutical agent as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (polyfluoro copolymer only) topcoat of the same polyfluoro copolymer used to provide sustained release of the drug or another polyfluoro copolymer that further restricts the diffusion of the drug out of the coating may be applied. The topcoat may be applied by dip coating with mandrel to clear the slots. This method is disclosed in U.S. Pat. No. 6,153,252. Other methods for applying the topcoat include spin coating and spray coating. Dip coating of the topcoat can be problematic if the drug is very soluble in the coating solvent, which swells the polyfluoro copolymer, and the clear coating solution acts as a zero concentration sink and redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001 percent to about seventy percent of the total coating weight, more typically about 0.001 percent to about sixty percent of the total coating weight. It is possible that the drug may represent as little as 0.0001 percent of the total coating weight.

The quantity and type of polyfluoro copolymers employed in the coating film comprising the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say approximately one to two-thousand hours, preferably two to eight-hundred hours) of effective amounts (0.001 µg/cm$^2$-min to 1000 µg/cm$^2$-min) of the drug. The dosage may be tailored to the subject being treated, the severity of the affliction, the judgment of the prescribing physician, and the like.

Individual formulations of drugs and polyfluoro copolymers may be tested in appropriate in vitro and in vivo models to achieve the desired drug release profiles. For example, a drug could be formulated with a polyfluoro copolymer, or blend of polyfluoro copolymers, coated onto a stent and placed in an agitated or circulating fluid system, for example, twenty-five percent ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in appropriate animal system. The drug release profile could then be monitored by appropriate means such as, by taking samples at specific times and assaying the samples for drug concentration (using HPLC to detect drug concentration). Thrombus formation can be modeled in animal models using the In-platelet imaging methods described by Hanson and Harker, Proc. Natl. Acad. Sci. USA 85:3184–3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those exemplary embodiments utilizing crosslinked films comprising pharmaceutical agents, curing may affect the rate at which the drug diffuses from the coating. Crosslinked polyfluoro copolymers films and coatings of the present invention also may be used without drug to modify the surface of implantable medical devices.

EXAMPLES

Example 1

A PVDF homopolymer (Solef® 1008 from Solvay Advanced Polymers, Houston, Tex., Tm about 175° C.) and polyfluoro copolymers of poly(vinylidenefluoride/HFP), 92/8 and 91/9 weight percent vinylidenefluoride/HFP as determined by F$^{19}$ NMR, respectively (eg: Solef® 11010 and 11008, Solvay Advanced Polymers, Houston, Tex., Tm about 159 degrees C. and 160 degrees C., respectively) were examined as potential coatings for stents. These polymers are soluble in solvents such as, but not limited to, DMAc, N,N-dimethylformamide (DMF), dimethyl sulfoxide (DMSO), N-methylpyrrolidone (NMP), tetrahydrofuran (THF) and acetone. Polymer coatings were prepared by dissolving the polymers in acetone, at five weight percent as a primer, or by dissolving the polymer in 50/50 DMAc/acetone, at thirty weight percent as a topcoat. Coatings that were applied to the stents by dipping and dried at 60 degrees C. in air for several hours, followed by 60 degrees C. for three hours in a <100 mm Hg vacuum, resulted in white foamy films. As applied, these films adhered poorly to the stent and flaked off, indicating they were too brittle. When stents coated in this manner were heated above 175 degrees C., i.e. above the melting temperature of the polymer, a clear, adherent film was formed. Since coatings require high temperatures, for example, above the melting temperature of the polymer, to achieve high quality films. As mentioned above, the high temperature heat treatment is unacceptable for the majority of drug compounds due to their thermal sensitivity.

Example 2

A polyfluoro copolymer (Solef® 21508) comprising 85.5 weight percent vinylidenefluoride copolymerized with 14.5 weight percent HFP, as determined by F$^{19}$ NMR, was evaluated. This copolymer is less crystalline than the polyfluoro homopolymer and copolymers described in Example 1. It also has a lower melting point reported to be about 133 degrees C. Once again, a coating comprising about twenty weight percent of the polyfluoro copolymer was applied from a polymer solution in 50/50 DMAc/MEK. After drying (in air) at 60 degrees C. for several hours, followed by 60 degrees C. for three hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process above was repeated, this time with a coating comprising the 85.5/14.6 (wt/wt) (vinylidenefluoride/HFP) and about thirty weight percent of rapamycin (Wyeth-Ayerst Laboratories, Philadelphia, Pa.), based on total weight of coating solids. Clear films that would occasionally crack or peel upon expansion of the coated stents resulted. It is believed that inclusion of plasticizers and the like in the coating composition will result in coatings and films for use on stents and other medical devices that are not susceptible to such cracking and peeling.

Example 3

Polyfluoro copolymers of still higher HFP content were then examined. This series of polymers were not semicrystalline, but rather are marketed as elastomers. One such copolymer is Fluorel™ FC2261Q (from Dyneon, a 3MHoechst Enterprise, Oakdale, Minn.), a 60.6/39.4 (wt/wt) copolymer of vinylidenefluoride/HFP. Although this copolymer has a Tg well below room temperature (Tg about minus twenty degrees C) it is not tacky at room temperature or even at sixty degrees C. This polymer has no detectable crystallinity when measured by Differential Scanning Calorimetry (DSC) or by wide angle X-ray diffraction. Films formed on stents as described above were non-tacky, clear, and expanded without incident when the stents were expanded.

The coating process above was repeated, this time with coatings comprising the 60.6/39.4 (wt/wt) (vinylidenefluoride/HFP) and about nine, thirty and fifty weight percent of rapamycin (Wyeth-Ayerst Laboratories, Philadelphia, Pa.), based on total weight of coating solids, respectively. Coatings comprising about nine and thirty weight percent rapamycin provided white, adherent, tough films that expanded without incident on the stent. Inclusion of fifty percent drug, in the same manner, resulted in some loss of adhesion upon expansion.

Changes in the comonomer composition of the polyfluoro copolymer also can affect the nature of the solid state coating, once dried. For example, the semicrystalline copolymer, Solef® 21508, containing 85.5 percent vinylidenefluoride polymerized with 14.5 percent by weight HFP forms homogeneous solutions with about 30 percent rapamycin (drug weight divided by total solids weight, for example, drug plus copolymer) in DMAc and 50/50 DMAc/MEK. When the film is dried (60 degrees C./16 hours followed by 60 degrees C./3 hours in vacuum of 100 mm Hg) a clear coating, indicating a solid solution of the drug in the polymer, is obtained. Conversely, when an amorphous copolymer, Fluorel™ FC2261Q, of PDVF/HFP at 60.6/39.5 (wt/wt) forms a similar thirty percent solution of rapamycin in DMAc/MEK and is similarly dried, a white film, indicating phase separation of the drug and the polymer, is obtained. This second drug containing film is much slower to release the drug into an in vitro test solution of twenty-five percent ethanol in water than is the former clear film of crystalline Solef® 21508. X-ray analysis of both films indicates that the drug is present in a non-crystalline form. Poor or very low solubility of the drug in the high HFP containing copolymer results in slow permeation of the drug through the thin coating film. Permeability is the product of diffusion rate of the diffusing species (in this case the drug) through the film (the copolymer) and the solubility of the drug in the film.

Example 4

In vitro Release Results of Rapamycin from Coating

Figure 3:
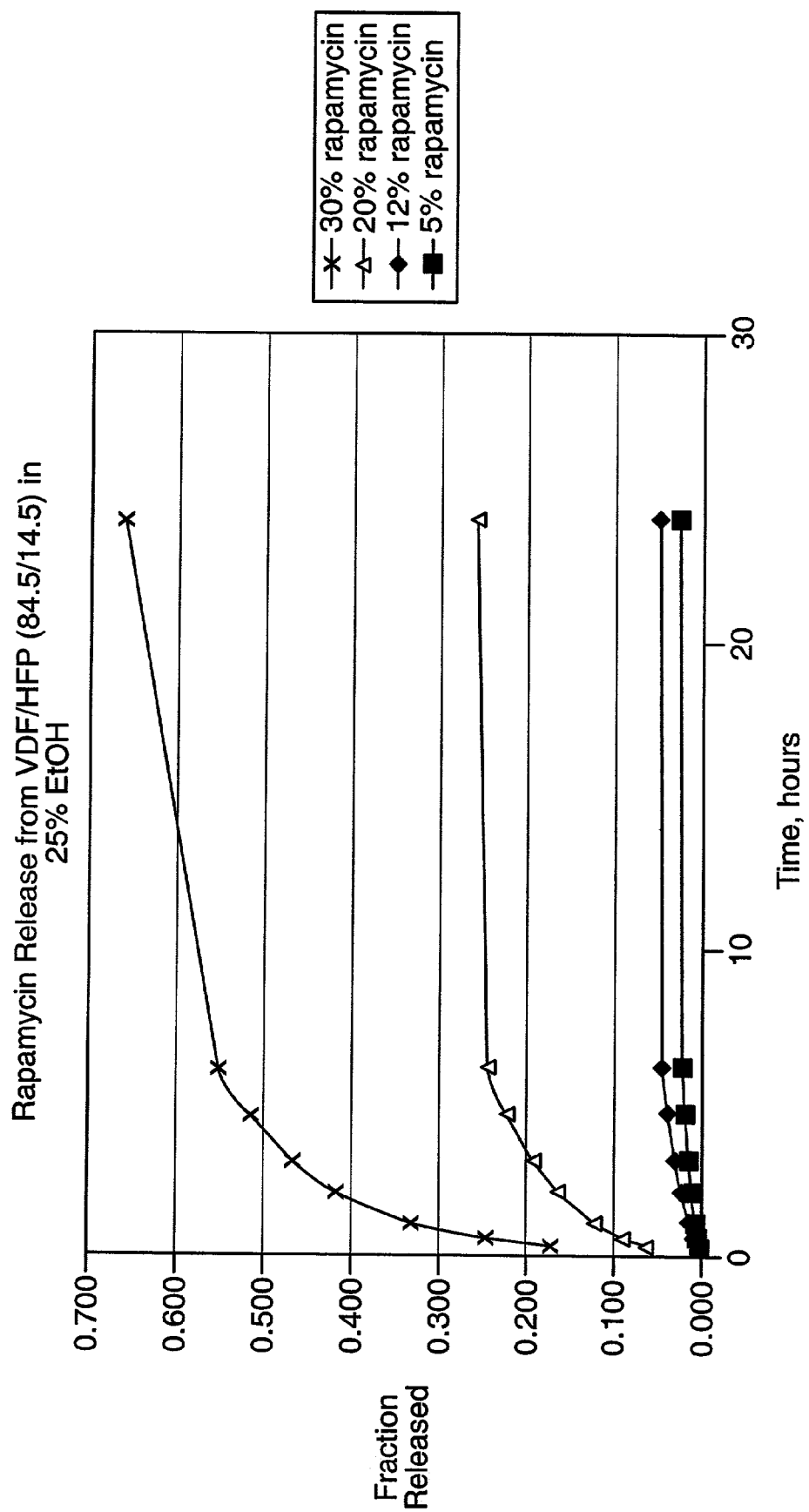
FIG. 3 indicates the fraction of drug released as a function of time from coatings of the present invention over which no topcoat has been disposed.
Figure 4:
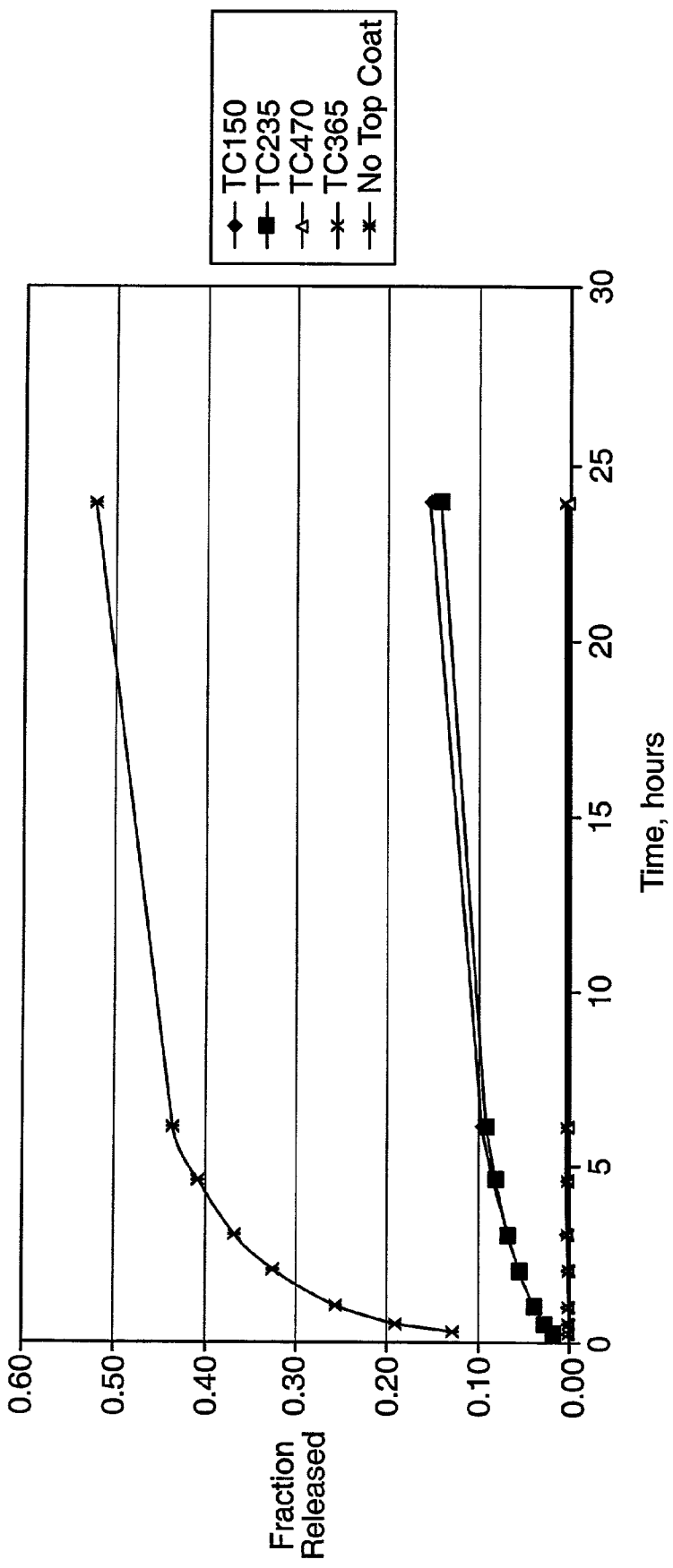
FIG. 4 indicates the fraction of drug released as a function of time from coatings of the present invention including a topcoat disposed thereon.
Figure 5:
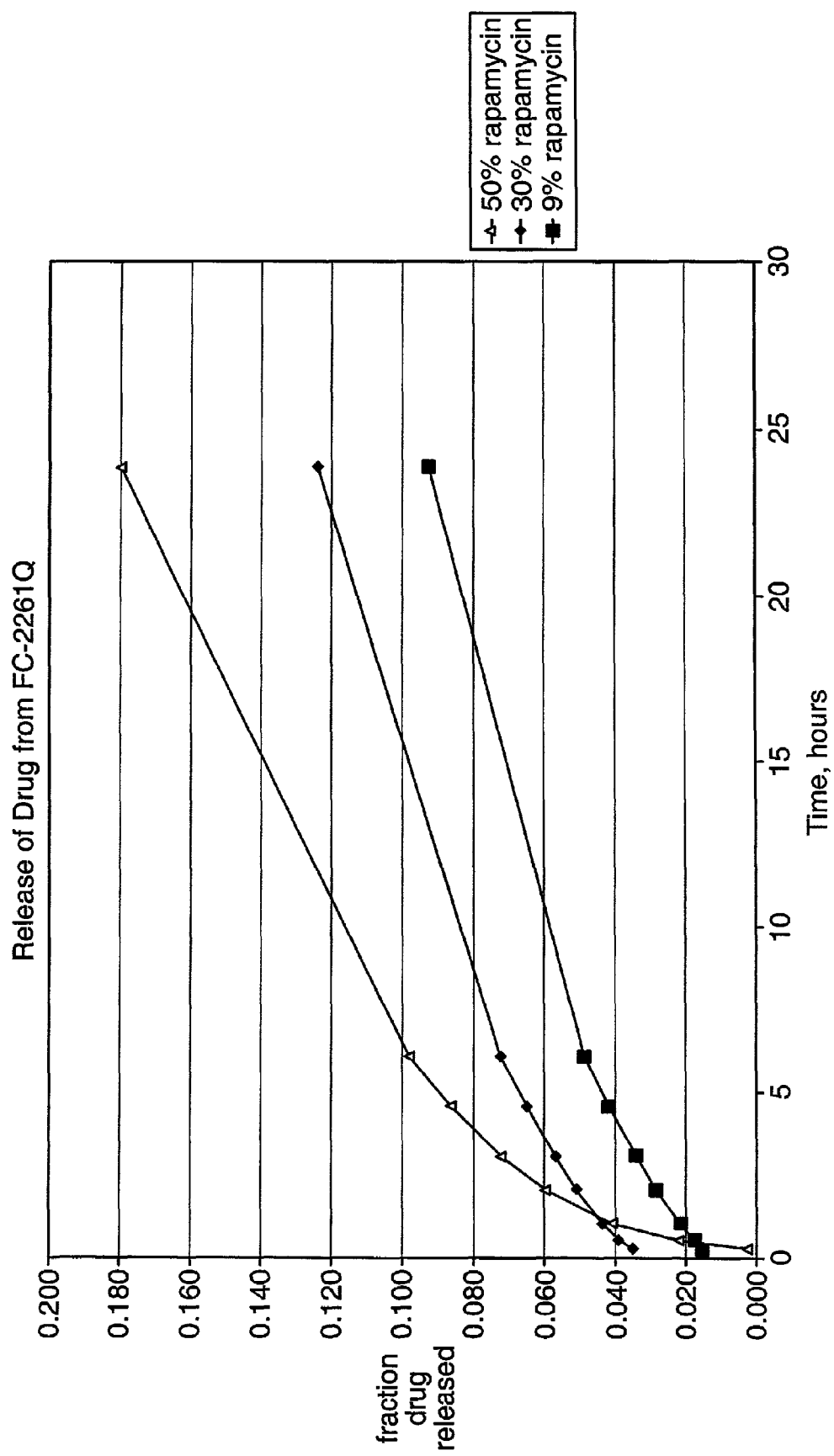
FIG. 5 indicates the fraction of drug released as a function of time from coatings of the present invention over which no topcoat has been disposed.
Figure 6:
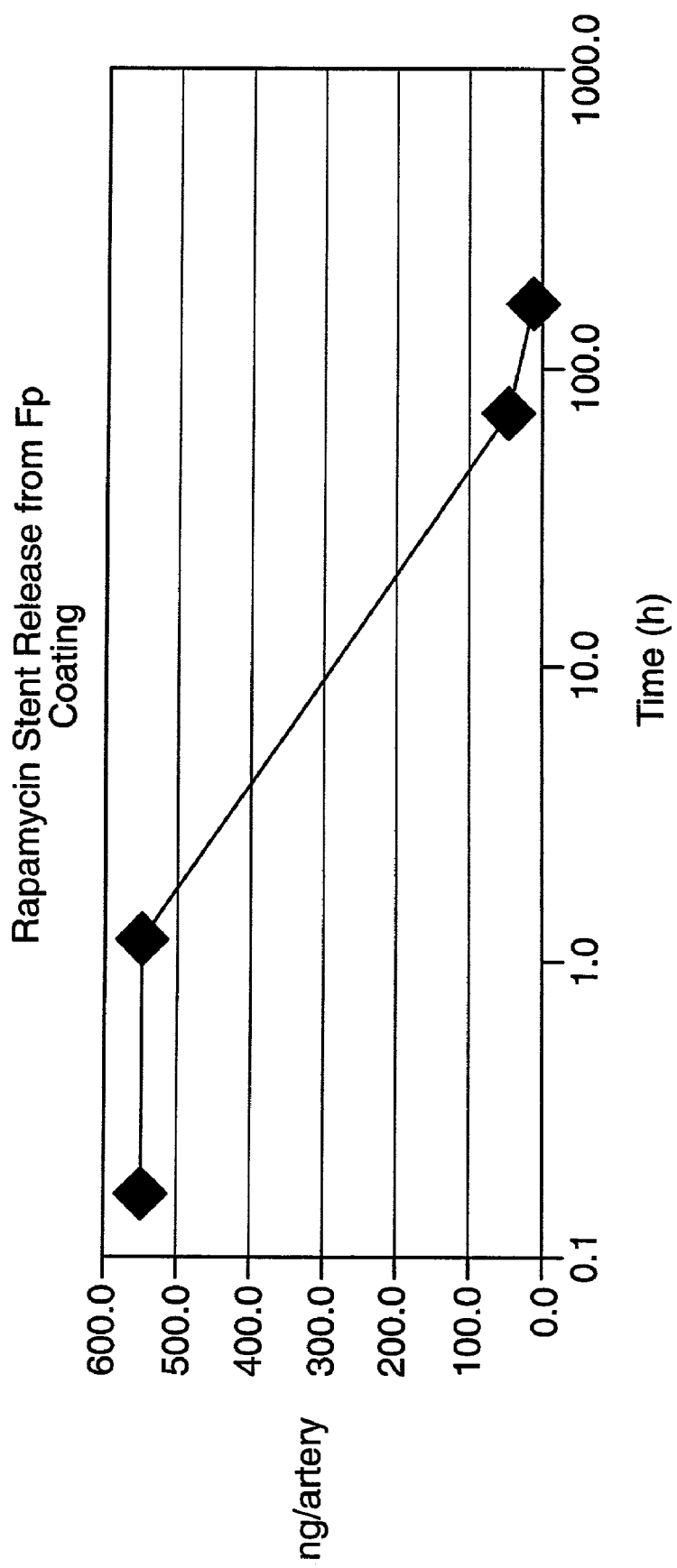
FIG. 6 indicates in vivo stent release kinetics of rapamycin from poly(VDF/HFP).

FIG. 3 is a plot of data for the 85.5/14.5 vinylidenefluoride/HFP polyfluoro copolymer, indicating fraction of drug released as a function of time, with no topcoat. FIG. 4 is a plot of data for the same polyfluoro copolymer over which a topcoat has been disposed, indicating that most effect on release rate is with a clear topcoat. As shown therein, TC150 refers to a device comprising one hundred fifty micrograms of topcoat, TC235 refers to two hundred thirty-five micrograms of topcoat, etc. The stents before topcoating had an average of seven hundred fifty micrograms of coating containing thirty percent rapamycin. FIG. 5 is a plot for the 60.6/39.4 vinylidenefluoride/HFP polyfluoro copolymer, indicating fraction of drug released as a function of time, showing significant control of release rate from the coating without the use of a topcoat. Release is controlled by loading of drug in the film.

Example 5

In vivo Stent Release Kinetics of Rapamycin from Poly(VDF/HFP)

Nine New Zealand white rabbits (2.5–3.0 kg) on a normal diet were given aspirin twenty-four hours prior to surgery, again just prior to surgery and for the remainder of the study. At the time of surgery, animals were premedicated with Acepromazine (0.1–0.2 mg/kg) and anesthetized with a KetaminelXylazine mixture (40 mg/kg and 5 mg/kg, respectively). Animals were given a single intraprocedural dose of heparin (150 IU/kg, i.v.)

Arteriectomy of the right common carotid artery was performed and a 5 F catheter introducer (Cordis, Inc.) placed in the vessel and anchored with ligatures. Iodine contrast agent was injected to visualize the right common carotid artery, brachlocephalic trunk and aortic arch. A steerable guide wire (0.014 inch/180 cm, Cordis, Inc.) was inserted via the introducer and advanced sequentially into each iliac artery to a location where the artery possesses a diameter closest to 2 mm using the angiographic mapping done previously. Two stents coated with a film made of poly (VDF/HFP): (60.6/39.4) with thirty percent rapamycin were deployed in each animal where feasible, one in each iliac artery, using 3.0 mm balloon and inflation to 8–10 ATM for thirty seconds followed after a one minute interval by a second inflation to 8–10 ATM for thirty seconds. Follow-up angiographs visualizing both iliac arteries are obtained to confirm correct deployment position of the stent.

At the end of procedure, the carotid artery was ligated and the skin is closed with 3/0 vicryl suture using a one layered interrupted closure. Animals were given butoropanol (0.4 mg/kg, s.c.) and gentamycin (4 mg/kg, i.m.). Following recovery, the animals were returned to their cages and allowed free access to food and water.

Due to early deaths and surgical difficulties, two animals were not used in this analysis. Stented vessels were removed from the remaining seven animals at the following time points: one vessel (one animal) at ten minutes post implant; six vessels (three animals) between forty minutes and two hours post-implant (average, 1.2 hours); two vessels (two animals) at three days post implant; and two vessels (one animal) at seven days post-implant. In one animal at two hours, the stent was retrieved from the aorta rather than the iliac artery. Upon removal, arteries were carefully trimmed at both the proximal and distal ends of the stent. Vessels were then carefully dissected free of the stent, flushed to remove any residual blood, and both stent and vessel frozen immediately, wrapped separately in foil, labeled and kept frozen at minus eighty degrees C. When all samples had been collected, vessels and stents were frozen, transported and subsequently analyzed for rapamycin in tissue and results are illustrated in FIG. 4.

Example 6

Purifying the Polymer

The Fluorel™ FC2261Q copolymer was dissolved in MEK at about ten weight percent and was washed in a 50/50 mixture of ethanol/water at a 14:1 of ethanol/water to the MEK solution ratio. The polymer precipitated out and was separated from the solvent phase by centrifugation. The polymer again was dissolved in MEK and the washing procedure repeated. The polymer was dried after each washing step at sixty degrees C. in a vacuum oven (<200 mtorr) over night.

Example 7

In vivo Testing of Coated Stents in Porcine Coronary Arteries

CrossFlex® stents (available from Cordis, a Johnson & Johnson Company) were coated with the "as received" Fluorel™ FC2261Q PVDF copolymer and with the purified polyfluoro copolymer of Example 6, using the dip and wipe approach. The coated stents were sterilized using ethylene oxide and a standard cycle. The coated stents and bare metal stents (controls) were implanted in porcine coronary arteries, where they remained for twenty-eight days.

Angiography was performed on the pigs at implantation and at twenty-eight days. Angiography indicated that the control uncoated stent exhibited about twenty-one percent restenosis. The polyfluoro copolymer "as received" exhibited about twenty-six percent restenosis(equivalent to the control) and the washed copolymer exhibited about 12.5 percent restenosis.

Histology results reported neointimal area at twenty-eight days to be 2.89±0.2, 3.57±0.4 and 2.75±0.3, respectively, for the bare metal control, the unpurified copolymer and the purified copolymer.

Since rapamycin acts by entering the surrounding tissue, it is preferably only affixed to the surface of the stent making contact with one tissue. Typically, only the outer surface of the stent makes contact with the tissue. Accordingly, in one exemplary embodiment, only the outer surface of the stent is coated with rapamycin.

The circulatory system, under normal conditions, has to be self-sealing, otherwise continued blood loss from an injury would be life threatening. Typically, all but the most catastrophic bleeding is rapidly stopped though a process known as hemostasis. Hemostasis occurs through a progression of steps. At high rates of flow, hemostasis is a combination of events involving platelet aggregation and fibrin formation. Platelet aggregation leads to a reduction in the blood flow due to the formation of a cellular plug while a cascade of biochemical steps leads to the formation of a fibrin clot.

Fibrin clots, as stated above, form in response to injury. There are certain circumstances where blood clotting or clotting in a specific area may pose a health risk. For example, during percutaneous transluminal coronary angioplasty, the endothelial cells of the arterial walls are typically injured, thereby exposing the sub-endothelial cells. Platelets adhere to these exposed cells. The aggregating platelets and the damaged tissue initiate further biochemical process resulting in blood coagulation. Platelet and fibrin blood clots may prevent the normal flow of blood to critical areas. Accordingly, there is a need to control blood clotting in various medical procedures. Compounds that do not allow blood to clot are called anti-coagulants. Essentially, an anticoagulant is an inhibitor of thrombin formation or function. These compounds include drugs such as heparin and hirudin. As used herein, heparin includes all direct or indirect inhibitors of thrombin or Factor Xa.

In addition to being an effective anti-coagulant, heparin has also been demonstrated to inhibit smooth muscle cell growth in vivo. Thus, heparin may be effectively utilized in conjunction with rapamycin in the treatment of vascular disease. Essentially, the combination of rapamycin and heparin may inhibit smooth muscle cell growth via two different mechanisms in addition to the heparin acting as an anti-coagulant.

Because of its multifunctional chemistry, heparin may be immobilized or affixed to a stent in a number of ways. For example, heparin may be immobilized onto a variety of surfaces by various methods, including the photolink methods set forth in U.S. Pat. Nos. 3,959,078 and 4,722,906 to Guire et al. and U.S. Pat. Nos. 5,229,172; 5,308,641; 5,350,800 and 5,415,938 to Cahalan et al. Heparinized surfaces have also been achieved by controlled release from a polymer matrix, for example, silicone rubber, as set forth in U.S. Pat. Nos. 5,837,313; 6,099,562 and 6,120,536 to Ding et al.

Unlike rapamycin, heparin acts on circulating proteins in the blood and heparin need only make contact with blood to be effective. Accordingly, if used in conjunction with a medical device, such as a stent, it would preferably be only on the side that comes into contact with the blood. For example, if heparin were to be administered via a stent, it would only have to be on the inner surface of the stent to be effective.

Figure 7:
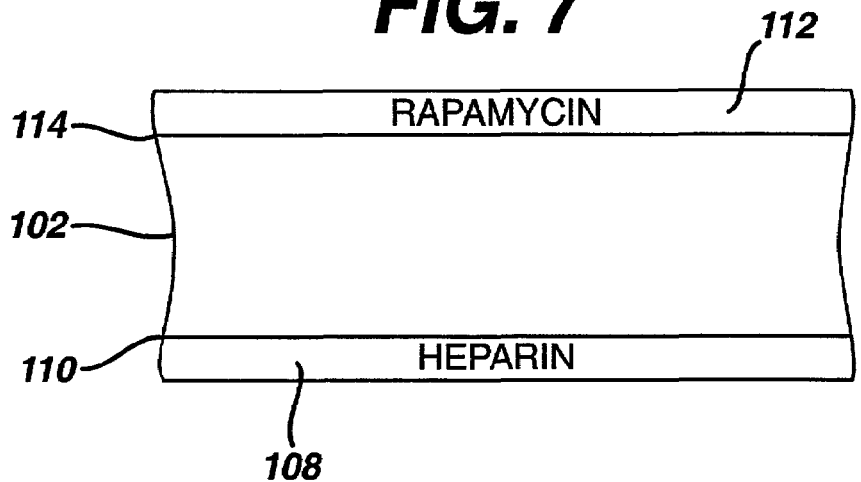
FIG. 7 is a cross-sectional view of a band of the stent of FIG. 1 having drug coatings thereon in accordance with a first exemplary embodiment of the invention.

In an exemplary embodiment of the invention, a stent may be utilized in combination with rapamycin and heparin to treat vascular disease. In this exemplary embodiment, the heparin is immobilized to the inner surface of the stent so that it is in contact with the blood and the rapamycin is immobilized to the outer surface of the stent so that it is in contact with the surrounding tissue. FIG. 7 illustrates a cross-section of a band 102 of the stent 100 illustrated in FIG. 1. As illustrated, the band 102 is coated with heparin 108 on its inner surface 110 and with rapamycin 112 on its outer surface 114.

Figure 8:
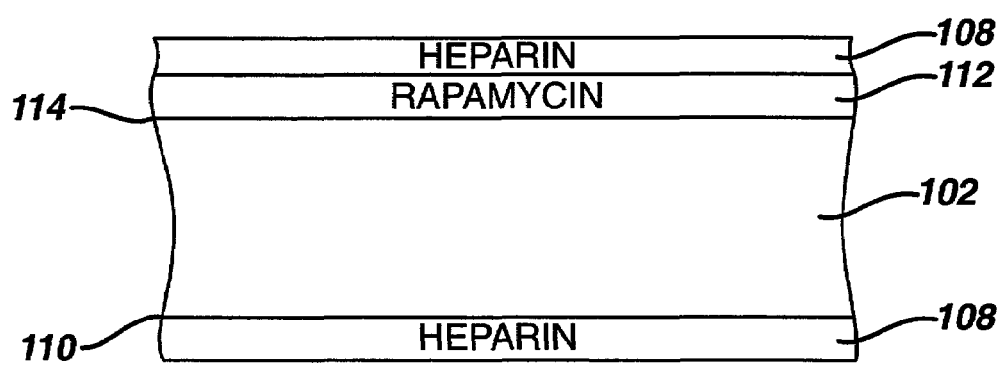
FIG. 8 is a cross-sectional view of a band of the stent of FIG. 1 having drug coatings thereon in accordance with a second exemplary embodiment of the invention.

In an alternate exemplary embodiment, the stent may comprise a heparin layer immobilized on its inner surface, and rapamycin and heparin on its outer surface. Utilizing current coating techniques, heparin tends to form a stronger bond with the surface it is immobilized to then does rapamycin. Accordingly, it may be possible to first immobilize the rapamycin to the outer surface of the stent and then immobilize a layer of heparin to the rapamycin layer. In this embodiment, the rapamycin may be more securely affixed to the stent while still effectively eluting from its polymeric matrix, through the heparin and into the surrounding tissue. FIG. 8 illustrates a cross-section of a band 102 of the stent 100 illustrated in FIG. 1. As illustrated, the band 102 is coated with heparin 108 on its inner surface 110 and with rapamycin 112 and heparin 108 on its outer surface 114.

Figure 9:
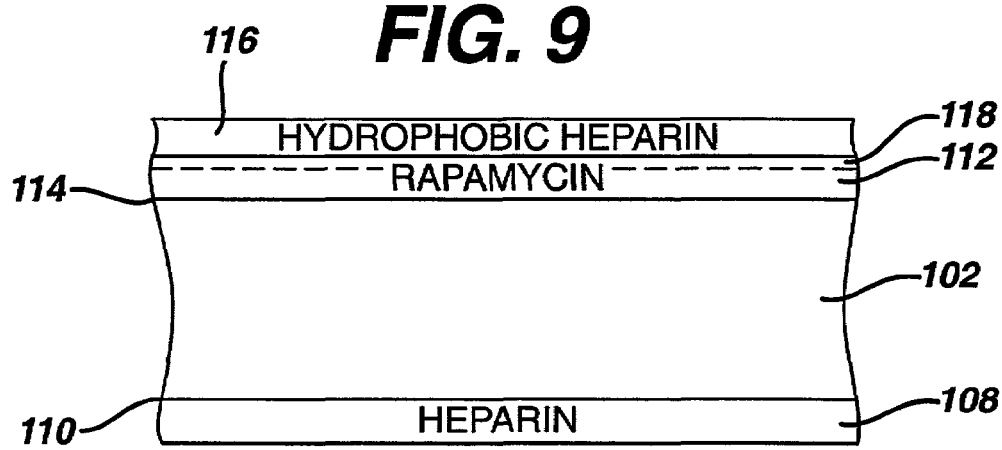
FIG. 9 is a cross-sectional view of a band of the stent of FIG. 1 having drug coatings thereon in accordance with a third exemplary embodiment of the present invention.

There are a number of possible ways to immobilize, i.e., entrapment or covalent linkage with an erodible bond, the heparin layer to the rapamycin layer. For example, heparin may be introduced into the top layer of the polymeric matrix. In other embodiments, different forms of heparin may be directly immobilized onto the top coat of the polymeric matrix, for example, as illustrated in FIG. 9. As illustrated, a hydrophobic heparin layer 116 may be immobilized onto the top coat layer 118 of the rapamycin layer 112. A hydrophobic form of heparin is utilized because rapamycin and heparin coatings represent incompatible coating application technologies. Rapamycin is an organic solvent-based coating and heparin, in its native form, is a water-based coating.

As stated above, a rapamycin coating may be applied to stents by a dip, spray or spin coating method, and/or any combination of these methods. Various polymers may be utilized. For example, as described above, poly(ethylene-co-vinyl acetate) and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. Also as described above, barrier or top coatings may also be applied to modulate the dissolution of rapamycin from the polymer matrix. In the exemplary embodiment described above, a thin layer of heparin is applied to the surface of the polymeric matrix. Because these polymer systems are hydrophobic and incompatible with the hydrophilic heparin, appropriate surface modifications may be required.

The application of heparin to the surface of the polymeric matrix may be performed in various ways and utilizing various biocompatible materials. For example, in one embodiment, in water or alcoholic solutions, polyethylene imine may be applied on the stents, with care not to degrade the rapamycin (e.g., pH<7, low temperature), followed by the application of sodium heparinate in aqueous or alcoholic solutions. As an extension of this surface modification, covalent heparin may be linked on polyethylene imine using amide-type chemistry (using a carbondiimide activator, e.g. EDC) or reductive amination chemistry (using CBAS-heparin and sodium cyanoborohydride for coupling). In another exemplary embodiment, heparin may be photolinked on the surface, if it is appropriately grafted with photo initiator moieties. Upon application of this modified heparin formulation on the covalent stent surface, light exposure causes cross-linking and immobilization of the heparin on the coating surface. In yet another exemplary embodiment, heparin may be complexed with hydrophobic quaternary ammonium salts, rendering the molecule soluble in organic solvents (e.g. benzalkonium heparinate, troidodecylmethylammonium heparinate). Such a formulation of heparin may be compatible with the hydrophobic rapamycin coating, and may be applied directly on the coating surface, or in the rapamycin/hydrophobic polymer formulation.

It is important to note that the stent, as described above, may be formed from any number of materials, including various metals, polymeric materials and ceramic materials. Accordingly, various technologies may be utilized to immobilize the various drugs, agent, compound combinations thereon. Specifically, in addition to the polymeric matricies, described above, biopolymers may be utilized. Biopolymers may be generally classified as natural polymers, while the above-described polymers may be described as synthetic polymers. Exemplary biopolymers, which may be utilized include agarose, alginate, gelatin, collagen and elastin. In addition, the drugs, agents or compounds may be utilized in conjunction with other percutaneously delivered medical devices such as grafts and perfusion balloons.

In addition to utilizing an anti-proliferative and anti-coagulant, anti-inflammatories may also be utilized in combination therewith. One example of such a combination would be the addition of an anti-inflammatory corticosteroid such as dexamethasone with an anti-proliferative, such as rapamycin, cladribine, vincristine, taxol, or a nitric oxide donor and an anti-coagulant, such as heparin. Such combination therapies might result in a better therapeutic effect, i.e., less proliferation as well as less inflammation, a stimulus for proliferation, than would occur with either agent alone. The delivery of a stent comprising an anti-proliferative, anti-coagulant, and an anti-inflammatory to an injured vessel would provide the added therapeutic benefit of limiting the degree of local smooth muscle cell proliferation, reducing a stimulus for proliferation, i.e., inflammation and reducing the effects of coagulation thus enhancing the restenosis-limiting action of the stent.

In other exemplary embodiments of the inventions, growth factor inhibitor or cytokine signal transduction inhibitor, such as the ras inhibitor, R115777 or P38 kinase inhibitor RWJ67657, or a tyrosine kinase inhibitor, such as tyrphostin, might be combined with an anti-proliferative agent such as taxol, vincristine or rapamycin so that proliferation of smooth muscle cells could be inhibited by different mechanisms. Alternatively, an anti-proliferative agent such as taxol, vincristine or rapamycin could be combined with an inhibitor of extracellular matrix synthesis such as halofuginone. In the above cases, agents acting by different mechanisms could act synergistically to reduce smooth muscle cell proliferation and vascular hyperplasia. This invention is also intended to cover other combinations of two or more such drug agents. As mentioned above, such drugs, agents or compounds could be administered systemically, delivered locally via drug delivery catheter, or formulated for delivery from the surface of a stent, or given as a combination of systemic and local therapy.

In addition to anti-proliferatives, anti-inflammatories and anti-coagulants, other drugs, agents or compounds may be utilized in conjunction with the medical devices. For example, immunosuppressants may be utilized alone or in combination with these other drugs, agents or compounds. Also gene therapy delivery mechanisms such as modified genes (nucleic acids including recombinant DNA) in viral vectors and non-viral gene vectors such as plasmids may also be introduced locally via a medical device. In addition, the present invention may be utilized with cell based therapy.

In addition to all of the drugs, agents, compounds and modified genes described above, chemical agents that are not ordinarily therapeutically or biologically active may also be utilized in conjunction with the present invention. These chemical agents, commonly referred to as pro-drugs, are agents that become biologically active upon their introduction into the living organism by one or more mechanisms. These mechanisms include the addition of compounds supplied by the organism or the cleavage of compounds from the agents caused by another agent supplied by the organism. Typically, pro-drugs are more absorbable by the organism. In addition, pro-drugs may also provide some additional measure of time release.

The coatings and drugs, agents or compounds described above may be utilized in combination with any number of medical devices, and in particular, with implantable medical devices such as stents and stent-grafts. Other devices such as vena cava filters and anastomosis devices may be used with coatings having drugs, agents or compounds therein. The exemplary stent illustrated in FIGS. 1 and 2 is a balloon expandable stent. Balloon expandable stents may be utilized in any number of vessels or conduits, and are particularly well suited for use in coronary arteries. Self-expanding stents, on the other hand, are particularly well suited for use in vessels where crush recovery is a critical factor, for example, in the carotid artery. Accordingly, it is important to note that any of the drugs, agents or compounds, as well as the coatings described above, may be utilized in combination with self-expanding stents such as those described below.

Figure 10:
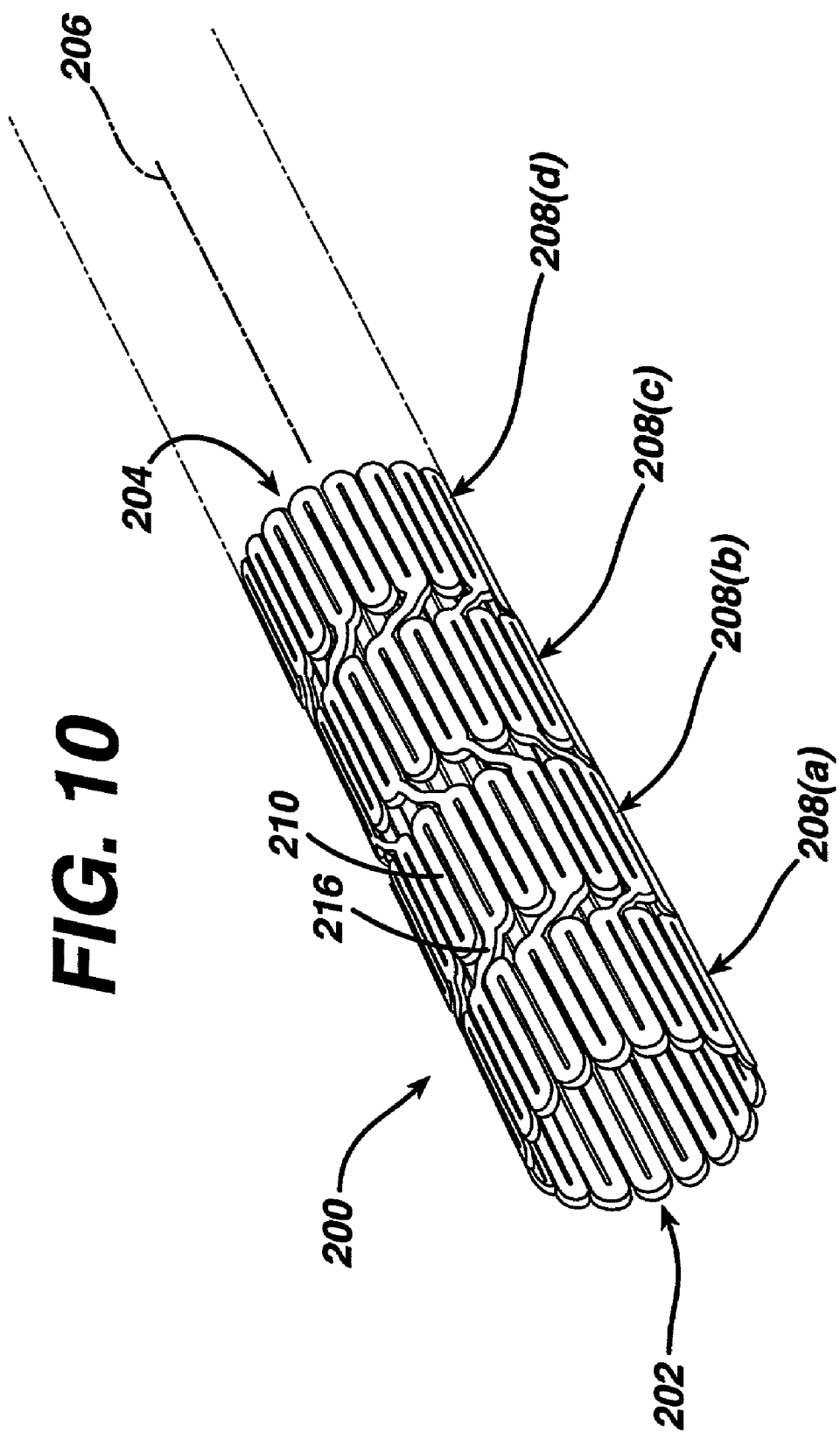
FIG. 10 is a perspective view of an exemplary stent in its compressed state which may be utilized in conjunction with the present invention.
Figure 11:
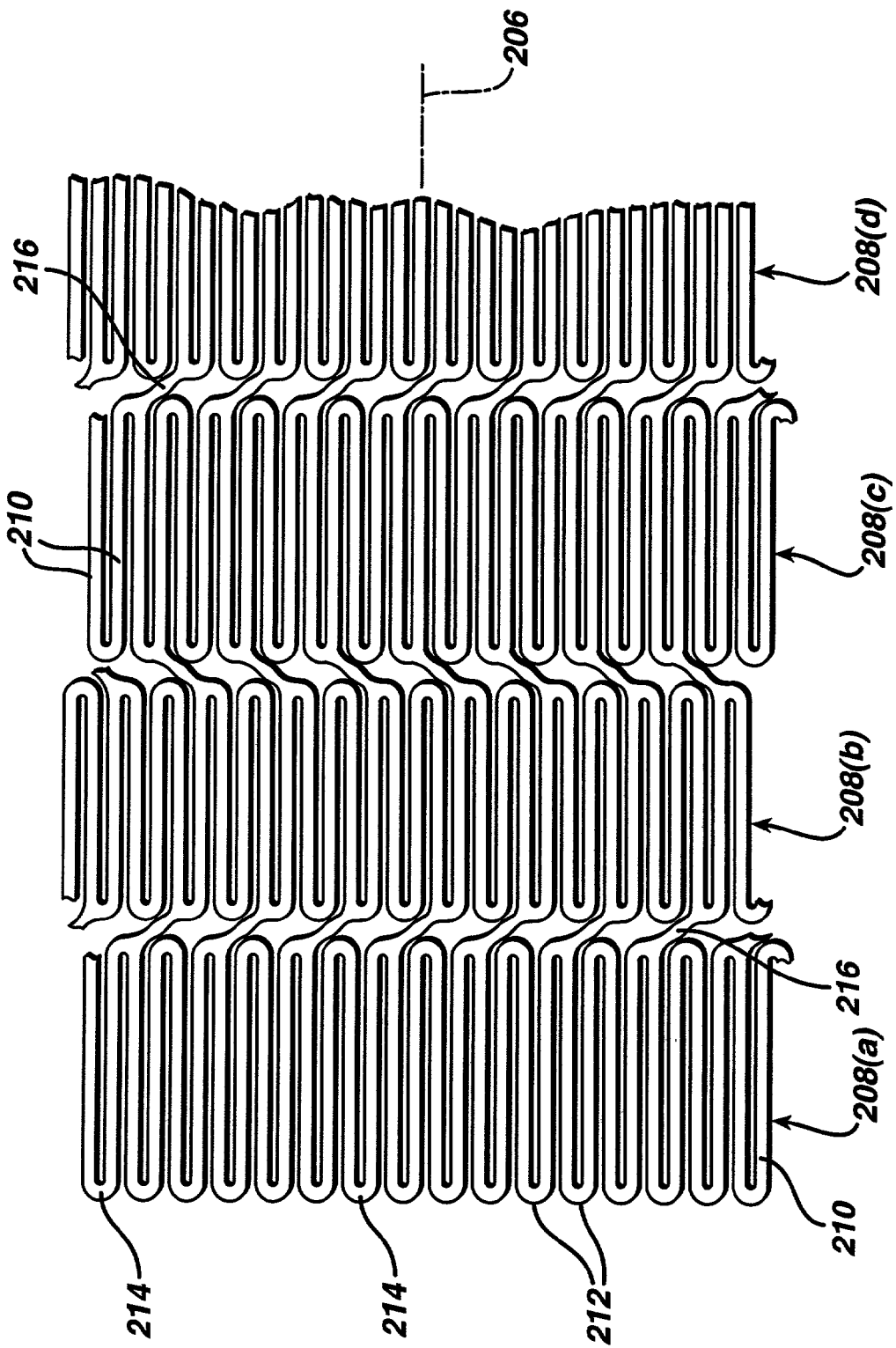
FIG. 11 is a sectional, flat view of the stent shown in FIG. 10.

There is illustrated in FIGS. 10 and 11, a stent 200, which may be utilized in connection with the present invention. FIGS. 10 and 11 illustrate the exemplary stent 200 in its unexpanded or compressed state. The stent 200 is preferably made from a superelastic alloy such as Nitinol. Most preferably, the stent 200 is made from an alloy comprising from about fifty percent (as used herein these percentages refer to weight percentages) Ni to about sixty percent Ni, and more preferably about 55.8 percent Ni, with the remainder of the alloy being Ti. Preferably, the stent 200 is designed such that it is superelastic at body temperature, and preferably has an Af in the range from about twenty-four degrees C. to about thirty-seven degrees C. The superelastic design of the stent 200 makes it crush recoverable which, as discussed above, makes it useful as a stent or frame for any number of vascular devices in different applications.

Stent 200 is a tubular member having front and back open ends 202 and 204 and a longitudinal axis 206 extending therebetween. The tubular member has a first smaller diameter, FIGS. 10 and 11, for insertion into a patient and navigation through the vessels, and a second larger diameter, FIGS. 12 and 13, for deployment into the target area of a vessel. The tubular member is made from a plurality of adjacent hoops 208, FIG. 10 showing hoops 208(a)-208(d), extending between the front and back ends 202 and 204. The hoops 208 include a plurality of longitudinal struts 210 and a plurality of loops 212 connecting adjacent struts, wherein adjacent struts are connected at opposite ends so as to form a substantially S or Z shape pattern. The loops 212 are curved, substantially semi-circular with symmetrical sections about their centers 214.

Figure 14:
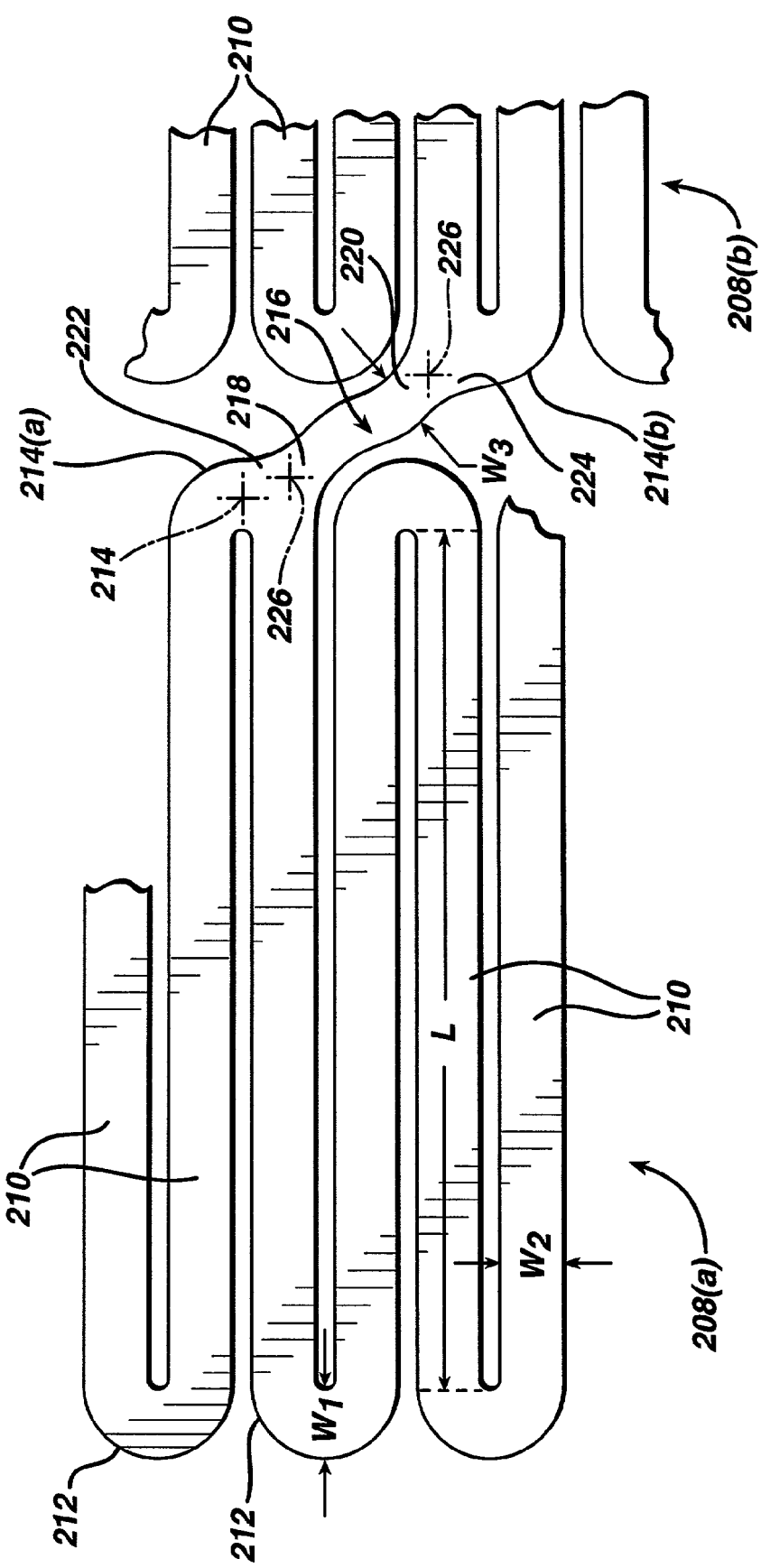
FIG. 14 is an enlarged view of section of the stent shown in FIG. 11.

Stent 200 further includes a plurality of bridges 216 which connect adjacent hoops 208 and which can best be described in detail by referring to FIG. 14. Each bridge 216 has two ends 218 and 220. The bridges 216 have one end attached to one strut and/or loop, and another end attached to a strut and/or loop on an adjacent hoop. The bridges 216 connect adjacent struts together at bridge to loop connection points 222 and 224. For example, bridge end 218 is connected to loop 214(a) at bridge to loop connection point 222, and bridge end 220 is connected to loop 214(b) at bridge to loop connection point 224. Each bridge to loop connection point has a center 226. The bridge to loop connection points are separated angularly with respect to the longitudinal axis. That is, the connection points are not immediately opposite each other. Essentially, one could not draw a straight line between the connection points, wherein such line would be parallel to the longitudinal axis of the stent.

The above described geometry helps to better distribute strain throughout the stent, prevents metal to metal contact when the stent is bent, and minimizes the opening size between the struts, loops and bridges. The number of and nature of the design of the struts, loops and bridges are important factors when determining the working properties and fatigue life properties of the stent. It was previously thought that in order to improve the rigidity of the stent, that struts should be large, and therefore there should be fewer struts per hoop. However, it has now been discovered that stents having smaller struts and more struts per hoop actually improve the construction of the stent and provide greater rigidity. Preferably, each hoop has between twenty-four to thirty-six or more struts. It has been determined that a stent having a ratio of number of struts per hoop to strut length L (in inches) which is greater than four hundred has increased rigidity over prior art stents, which typically have a ratio of under two hundred. The length of a strut is measured in its compressed state parallel to the longitudinal axis 206 of the stent 200 as illustrated in FIG. 10.

Figure 12:
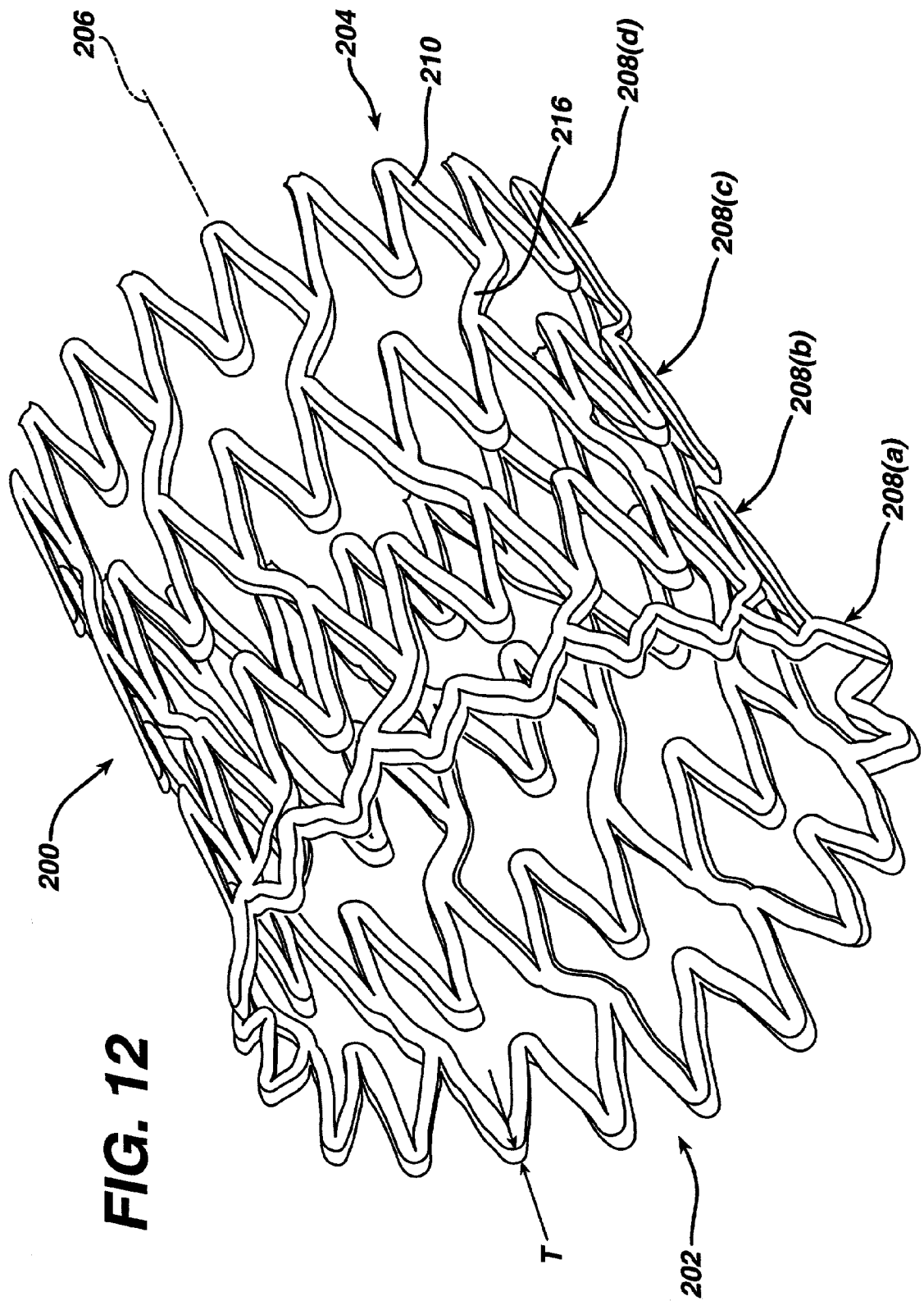
FIG. 12 is a perspective view of the stent shown in FIG. 10 but showing it in its expanded state.
Figure 13:
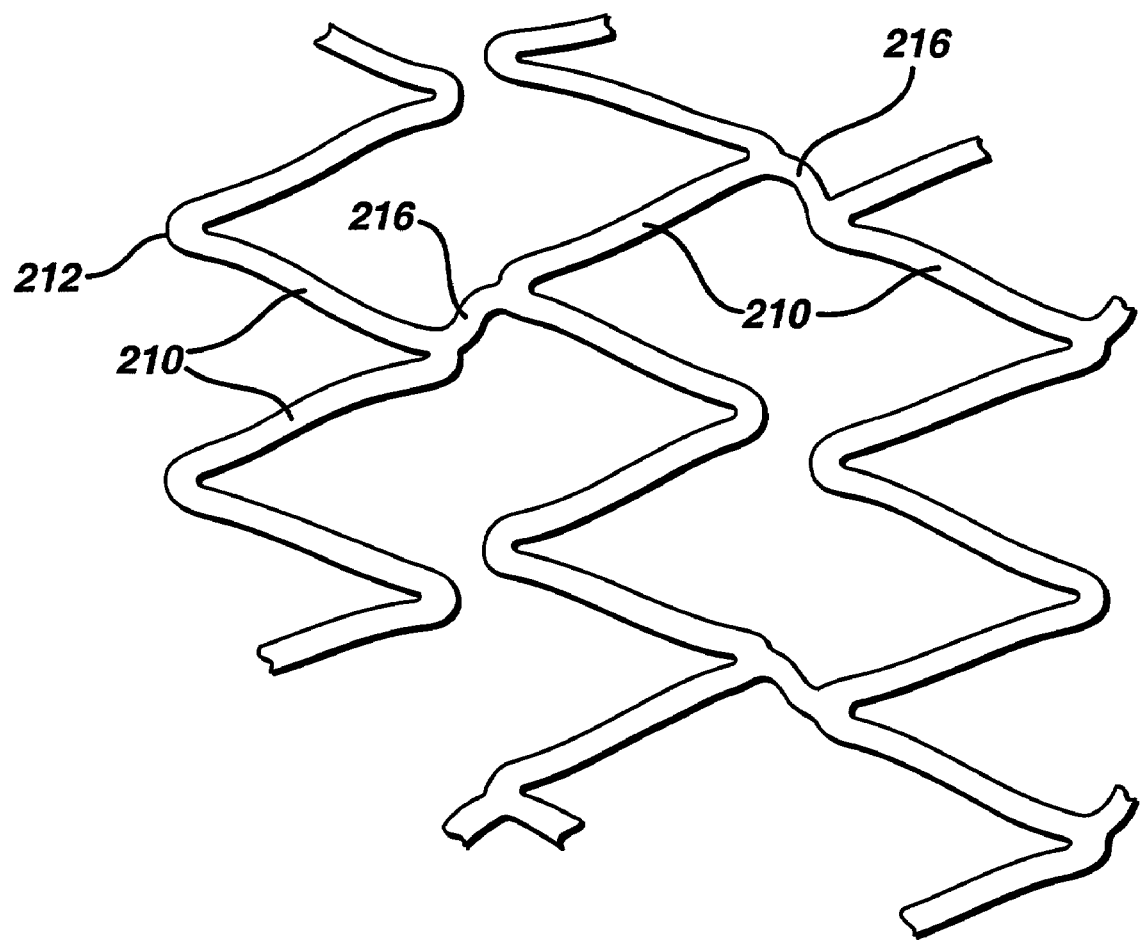
FIG. 13 is an enlarged sectional view of the stent shown in FIG. 12.

As seen from a comparison of FIGS. 10 and 12, the geometry of the stent 200 changes quite significantly as the stent 200 is deployed from its unexpanded state to its expanded state. As a stent undergoes diametric change, the strut angle and strain levels in the loops and bridges are affected. Preferably, all of the stent features will strain in a predictable manor so that the stent is reliable and uniform in strength. In addition, it is preferable to minimize the maximum strain experienced by struts loops and bridges, since Nitinol properties are more generally limited by strain rather than by stress. As will be discussed in greater detail below, the stent sits in the delivery system in its unexpanded state as shown in FIGS. 19 and 20. As the stent is deployed, it is allowed to expand towards its expanded state, as shown in FIG. 12, which preferably has a diameter which is the same or larger than the diameter of the target vessel. Nitinol stents made from wire deploy in much the same manner, and are dependent upon the same design constraints, as laser cut stents. Stainless steel stents deploy similarly in terms of geometric changes as they are assisted by forces from balloons or other devices.

In trying to minimize the maximum strain experienced by features of the stent, the present invention utilizes structural geometries which distribute strain to areas of the stent which are less susceptible to failure than others. For example, one of the most vulnerable areas of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and its ability to trap embolic material.

Many of these design objectives have been accomplished by an exemplary embodiment of the present invention, illustrated in FIGS. 10, 11 and 14. As seen from these figures, the most compact designs which maintain the largest radii at the loop to bridge connections are non-symmetric with respect to the centerline of the strut connecting loop. That is, loop to bridge connection point centers 226 are offset from the center 214 of the loops 212 to which they are attached. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni-Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

As seen in FIG. 14, stent 200 comprises strut connecting loops 212 having a width W1, as measured at the center 214 parallel to axis 206, which are greater than the strut widths W2, as measured perpendicular to axis 206 itself. In fact, it is preferable that the thickness of the loops vary so that they are thickest near their centers. This increases strain deformation at the strut and reduces the maximum strain levels at the extreme radii of the loop. This reduces the risk of stent failure and allows one to maximize radial strength properties. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. As stated above, this feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

As mentioned above, bridge geometry changes as a stent is deployed from its compressed state to its expanded state and vise-versa. As a stent undergoes diametric change, strut angle and loop strain is affected. Since the bridges are connected to either the loops, struts or both, they are affected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops being connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action may cause damage to the vessel.

However, one exemplary embodiment of the present invention, as illustrated in FIGS. 10 and 11, reduces the chance of such events happening when deploying the stent. By mirroring the bridge geometry longitudinally down the stent, the rotational shift of the Z-sections or S-sections may be made to alternate and will minimize large rotational changes between any two points on a given stent during deployment or constraint. That is, the bridges 216 connecting loop 208(b) to loop 208(c) are angled upwardly from left to right, while the bridges connecting loop 208(c) to loop 208(d) are angled downwardly from left to right. This alternating pattern is repeated down the length of the stent 200. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend to grow if twisted in one direction and shrink if twisted in the other direction. With alternating bridge slopes this effect is minimized and localized.

The feature is particularly advantageous for stents having large expansion ratios, which in turn requires them to have extreme bending requirements where large elastic strains are required. Nitinol, as stated above, can withstand extremely large amounts of elastic strain deformation, so the above features are well suited to stents made from this alloy. This feature allows for maximum utilization of Ni-Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Preferably, stents are laser cut from small diameter tubing. For prior art stents, this manufacturing process led to designs with geometric features, such as struts, loops and bridges, having axial widths W2, W1 and W3, respectively, which are larger than the tube wall thickness T (illustrated in FIG. 12). When the stent is compressed, most of the bending occurs in the plane that is created if one were to cut longitudinally down the stent and flatten it out. However, for the individual bridges, loops and struts, which have widths greater than their thickness, there is a greater resistance to this in-plane bending than to out-of-plane bending. Because of this, the bridges and struts tend to twist, so that the stent as a whole may bend more easily. This twisting is a buckling condition which is unpredictable and can cause potentially high strain.

However, this problem has been solved in an exemplary embodiment of the present invention, as illustrated in FIGS. 10–14. As seen from these figures, the widths of the struts, hoops and bridges are equal to or less than the wall thickness of the tube. Therefore, substantially all bending and, therefore, all strains are "out-of-plane." This minimizes twisting of the stent which minimizes or eliminates buckling and unpredictable strain conditions. This feature is particularly advantageous for stents having large expansion ratios, which in turn requires them to have extreme bending requirements where large elastic strains are required. Nitinol, as stated above, can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Figure 15:
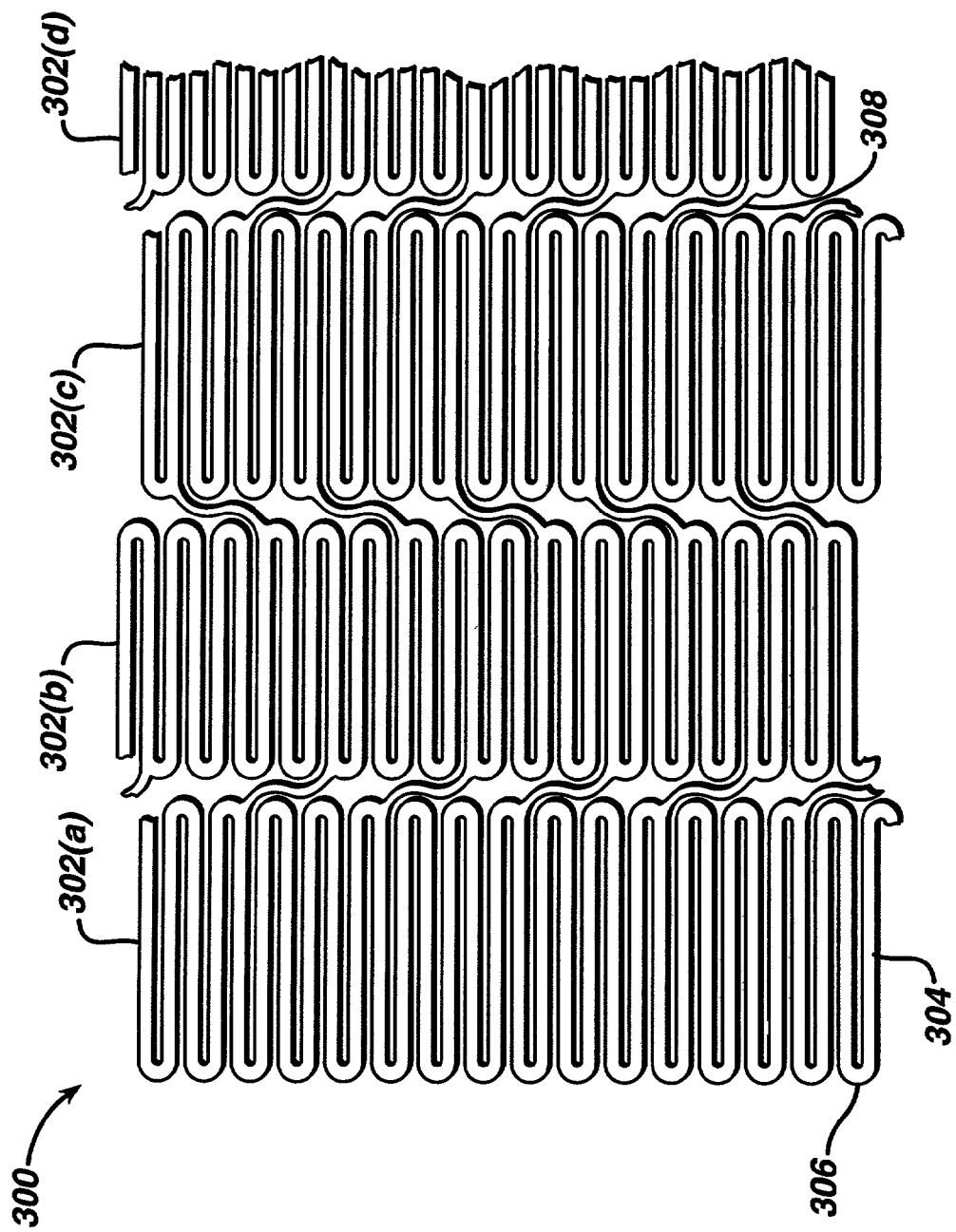
FIG. 15 is a view similar to that of FIG. 11 but showing an alternate embodiment of the stent.

An alternate exemplary embodiment of a stent that may be utilized in conjunction with the present invention is illustrated in FIG. 15. FIG. 15 shows stent 300 which is similar to stent 200 illustrated in FIGS. 10–14. Stent 300 is made from a plurality of adjacent hoops 302, FIG. 15 showing hoops 302(a)-302(d). The hoops 302 include a plurality of longitudinal struts 304 and a plurality of loops 306 connecting adjacent struts, wherein adjacent struts are connected at opposite ends so as to form a substantially S or Z shape pattern. Stent 300 further includes a plurality of bridges 308 which connect adjacent hoops 302. As seen from the figure, bridges 308 are non-linear and curve between adjacent hoops. Having curved bridges allows the bridges to curve around the loops and struts so that the hoops can be placed closer together which in turn, minimizes the maximum open area of the stent and increases its radial strength as well. This can best be explained by referring to FIG. 13. The above described stent geometry attempts to minimize the largest circle which could be inscribed between the bridges, loops and struts, when the stent is expanded. Minimizing the size of this theoretical circle, greatly improves the stent because it is then better suited to trap embolic material once it is inserted into the patient.

As mentioned above, it is preferred that the stent of the present invention be made from a superelastic alloy and most preferably made of an alloy material having greater than 50.5 atomic percentage Nickel and the balance Titanium. Greater than 50.5 atomic percentage Nickel allows for an alloy in which the temperature at which the martensite phase transforms completely to the austenite phase (the Af temperature) is below human body temperature, and preferably is about twenty-four degrees C. to about thirty-seven degrees C., so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent into the tube, as discussed above and as shown in the figures. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor which controls all aspects of the process. After the stent pattern is cut, the stent is treated and polished using any number of methods or combination of methods well known to those skilled in the art. Lastly, the stent is then cooled until it is completely martensitic, crimped down to its un-expanded diameter and then loaded into the sheath of the delivery apparatus.

Figure 16:
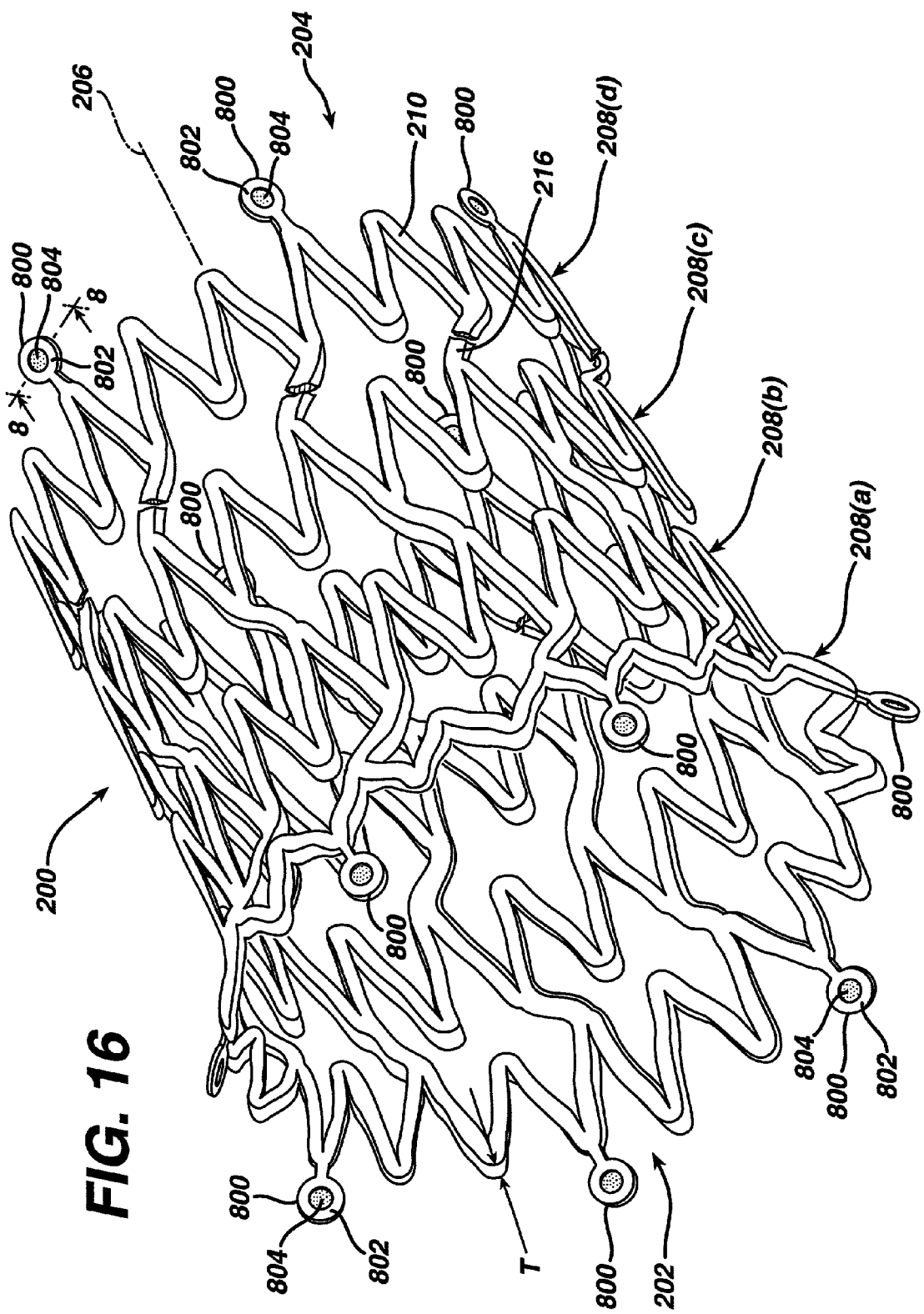
FIG. 16 is a perspective view of the stent of FIG. 10 having a plurality of markers attached to the ends thereof in accordance with the present invention.
Figure 17:
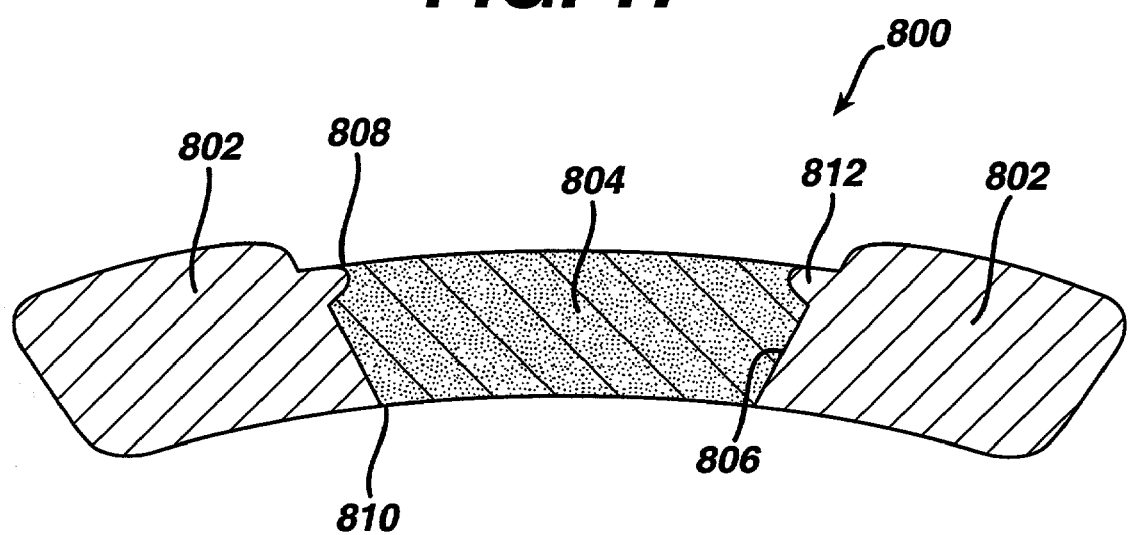
FIG. 17 is a cross-sectional view of a marker in accordance with the present invention.

As stated in previous sections of this application, markers having a radiopacity greater than that of the superelastic alloys may be utilized to facilitate more precise placement of the stent within the vasculature. In addition, markers may be utilized to determine when and if a stent is fully deployed. For example, by determining the spacing between the markers, one can determine if the deployed stent has achieved its maximum diameter and adjusted accordingly utilizing a tacking process. FIG. 16 illustrates an exemplary embodiment of the stent 200 illustrated in FIGS. 10–14 having at least one marker on each end thereof. In a preferred embodiment, a stent having thirty-six struts per hoop can accommodate six markers 800. Each marker 800 comprises a marker housing 802 and a marker insert 804. The marker insert 804 may be formed from any suitable biocompatible material having a high radiopacity under X-ray fluoroscopy. In other words, the marker inserts 804 should preferably have a radiopacity higher than that of the material comprising the stent 200. The addition of the marker housings 802 to the stent necessitates that the lengths of the struts in the last two hoops at each end of the stent 200 be longer than the strut lengths in the body of the stent to increase the fatigue life at the stent ends. The marker housings 802 are preferably cut from the same tube as the stent as briefly described above. Accordingly, the housings 802 are integral to the stent 200. Having the housings 802 integral to the stent 200 serves to ensure that the markers 800 do not interfere with the operation of the stent FIG. 17 is a cross-sectional view of a marker housing 802. The housing 802 may be elliptical when observed from the outer surface as illustrated in FIG. 16. As a result of the laser cutting process, the hole 806 in the marker housing 802 is conical in the radial direction with the outer surface 808 having a diameter larger than the diameter of the inner surface 810, as illustrated in FIG. 17. The conical tapering in the marker housing 802 is beneficial in providing an interference fit between the marker insert 804 and the marker housing 802 to prevent the marker insert 804 from being dislodged once the stent 200 is deployed. A detailed description of the process of locking the marker insert 804 into the marker housing 802 is given below.

As set forth above, the marker inserts 804 may be made from any suitable material having a radiopacity higher than the superelastic material forming the stent or other medical device. For example, the marker insert 804 may be formed from niobium, tungsten, gold, platinum or tantalum. In the preferred embodiment, tantalum is utilized because of its closeness to nickel-titanium in the galvanic series and thus would minimize galvanic corrosion. In addition, the surface area ratio of the tantalum marker inserts 804 to the nickel-titanium is optimized to provide the largest possible tantalum marker insert, easy to see, while minimizing the galvanic corrosion potential. For example, it has been determined that up to nine marker inserts 804 having a diameter of 0.010 inches could be placed at the end of the stent 200; however, these marker inserts 804 would be less visible under X-ray fluoroscopy. On the other hand, three to four marker inserts 804 having a diameter of 0.025 inches could be accommodated on the stent 200; however, galvanic corrosion resistance would be compromised. Accordingly, in the preferred embodiment, six tantalum markers having a diameter of 0.020 inches are utilized on each end of the stent 200 for a total of twelve markers 800.

The tantalum markers 804 may be manufactured and loaded into the housing utilizing a variety of known techniques. In the exemplary embodiment, the tantalum markers 804 are punched out from an annealed ribbon stock and are shaped to have the same curvature as the radius of the marker housing 802 as illustrated in FIG. 17. Once the tantalum marker insert 804 is loaded into the marker housing 802, a coining process is used to properly seat the marker insert 804 below the surface of the housing 802. The coining punch is also shaped to maintain the same radius of curvature as the marker housing 802. As illustrated in FIG. 17, the coining process deforms the marker housing 802 material to lock in the marker insert 804.

As stated above, the hole 806 in the marker housing 802 is conical in the radial direction with the outer surface 808 having a diameter larger than the diameter of the inner surface 810 as illustrated in FIG. 17. The inside and outside diameters vary depending on the radius of the tube from which the stent is cut. The marker inserts 804, as stated above, are formed by punching a tantalum disk from annealed ribbon stock and shaping it to have the same radius of curvature as the marker housing 802. It is important to note that the marker inserts 804, prior to positioning in the marker housing 804, have straight edges. In other words, they are not angled to match the hole 806. The diameter of the marker insert 804 is between the inside and outside diameter of the marker housing 802. Once the marker insert 804 is loaded into the marker housing, a coining process is used to properly seat the marker insert 804 below the surface of the housing 802. In the preferred embodiment, the thickness of the marker insert 804 is less than or equal to the thickness of the tubing and thus the thickness or height of the hole 806. Accordingly, by applying the proper pressure during the coining process and using a coining tool that is larger than the marker insert 804, the marker insert 804 may be seated in the marker housing 802 in such a way that it is locked into position by a radially oriented protrusion 812. Essentially, the applied pressure, and size and shape of the housing tool forces the marker insert 804 to form the protrusion 812 in the marker housing 802. The coining tool is also shaped to maintain the same radius of curvature as the marker housing. As illustrated in FIG. 17, the protrusion 812 prevents the marker insert 804 from becoming dislodged from the marker housing.

It is important to note that the marker inserts 804 are positioned in and locked into the marker housing 802 when the stent 200 is in its unexpanded state. This is due to the fact that it is desirable that the tube's natural curvature be utilized. If the stent were in its expanded state, the coining process would change the curvature due to the pressure or force exerted by the coining tool.

Figure 18:
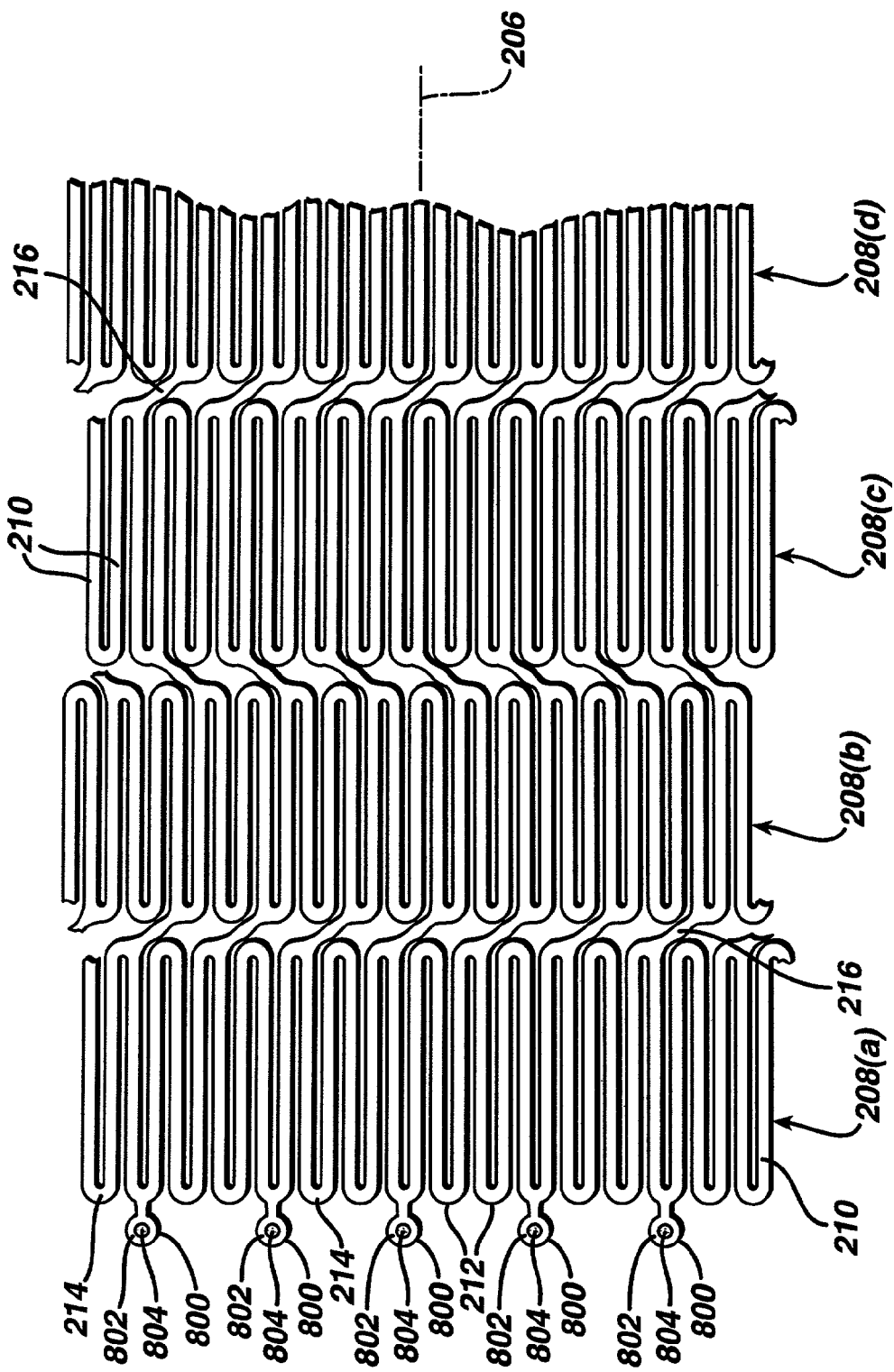
FIG. 18 is an enlarged perspective view of an end of the stent with the markers forming a substantially straight line in accordance with the present invention.

As illustrated in FIG. 18, the marker inserts 804 form a substantially solid line that clearly defines the ends of the stent in the stent delivery system when seen under fluoroscopic equipment. As the stent 200 is deployed from the stent delivery system, the markers 800 move away from each other and flower open as the stent 200 expands as illustrated in FIG. 16. The change in the marker grouping provides the physician or other health care provider with the ability to determine when the stent 200 has been fully deployed from the stent delivery system.

It is important to note that the markers 800 may be positioned at other locations on the stent 200.

It is believed that many of the advantages of the present invention can be better understood through a brief description of a delivery apparatus for the stent, as shown in FIGS. 19 and 20. FIGS. 19 and 20 show a self-expanding stent delivery apparatus 10 for a stent made in accordance with the present invention. Apparatus 10 comprises inner and outer coaxial tubes. The inner tube is called the shaft 12 and the outer tube is called the sheath 14. Shaft 12 has proximal and distal ends. The proximal end of the shaft 12 terminates at a luer lock hub 16. Preferably, shaft 12 has a proximal portion 18 which is made from a relatively stiff material such as stainless steel, Nitinol, or any other suitable material, and a distal portion 20 which may be made from a polyethylene, polyimide, Pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 20 of the shaft 12 has a distal tip 22 attached thereto. The distal tip 22 has a proximal end 24 whose diameter is substantially the same as the outer diameter of the sheath 14. The distal tip 22 tapers to a smaller diameter from its proximal end to its distal end, wherein the distal end 26 of the distal tip 22 has a diameter smaller than the inner diameter of the sheath 14. Also attached to the distal portion 20 of shaft 12 is a stop 28 which is proximal to the distal tip 22. Stop 28 may be made from any number of materials known in the art, including stainless steel, and is even more preferably made from a highly radiopaque material such as platinum, gold or tantalum. The diameter of stop 28 is substantially the same as the inner diameter of sheath 14, and would actually make frictional contact with the inner surface of the sheath. Stop 28 helps to push the stent out of the sheath during deployment, and helps keep the stent from migrating proximally into the sheath 14.

A stent bed 30 is defined as being that portion of the shaft between the distal tip 22 and the stop 28. The stent bed 30 and the stent 200 are coaxial so that the distal portion 20 of shaft 12 comprising the stent bed 30 is located within the lumen of the stent 200. However, the stent bed 30 does not make any contact with stent 200 itself. Lastly, shaft 12 has a guidewire lumen 32 extending along its length from its proximal end and exiting through its distal tip 22. This allows the shaft 12 to receive a guidewire much in the same way that an ordinary balloon angioplasty catheter receives a guidewire. Such guidewires are well known in art and help guide catheters and other medical devices through the vasculature of the body.

Sheath 14 is preferably a polymeric catheter and has a proximal end terminating at a sheath hub 40. Sheath 14 also has a distal end which terminates at the proximal end 24 of distal tip 22 of the shaft 12, when the stent is in its fully un-deployed position as shown in the figures. The distal end of sheath 14 includes a radiopaque marker band 34 disposed along its outer surface. As will be explained below, the stent is fully deployed from the delivery apparatus when the marker band 34 is lined up with radiopaque stop 28, thus indicating to the physician that it is now safe to remove the apparatus 10 from the body. Sheath 14 preferably comprises an outer polymeric layer and an inner polymeric layer. Positioned between outer and inner layers is a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993.

FIGS. 19 and 20 illustrate the stent 200 as being in its fully undeployed position. This is the position the stent is in when the apparatus 10 is inserted into the vasculature and its distal end is navigated to a target site. Stent 200 is disposed around stent bed 30 and at the distal end of sheath 14. The distal tip 22 of the shaft 12 is distal to the distal end of the sheath 14, and the proximal end of the shaft 12 is proximal to the proximal end of the sheath 14. The stent 200 is in a compressed state and makes frictional contact with the inner surface 36 of the sheath 14.

When being inserted into a patient, sheath 14 and shaft 12 are locked together at their proximal ends by a Tuohy Borst valve 38. This prevents any sliding movement between the shaft and sheath which could result in a premature deployment or partial deployment of the stent 200. When the stent 200 reaches its target site and is ready for deployment, the Tuohy Borst valve 38 is opened so that that the sheath 14 and shaft 12 are no longer locked together.

The method under which the apparatus 10 deploys the stent 200 is readily apparent. The apparatus 10 is first inserted into the vessel until the radiopaque stent markers 800 (front 202 and back 204 ends, see FIG. 16) are proximal and distal to the target lesion. Once this has occurred the physician would open the Tuohy Borst valve 38. The physician would then grasp hub 16 of shaft 12 SO as to hold it in place. Thereafter, the physician would grasp the proximal end of the sheath 14 and slide it proximal, relative to the shaft 12. Stop 28 prevents the stent 200 from sliding back with the sheath 14, SO that as the sheath 14 is moved back, the stent 200 is pushed out of the distal end of the sheath 14. As stent 200 is being deployed the radiopaque stent markers 800 move apart once they come out of the distal end of sheath 14. Stent deployment is complete when the marker 34 on the outer sheath 14 passes the stop 28 on the inner shaft 12. The apparatus 10 can now be withdrawn through the stent 200 and removed from the patient.

FIG. 21 illustrates the stent 200 in a partially deployed state. As illustrated, as the stent 200 expands from the delivery device 10, the markers 800 move apart from one another and expand in a flower like manner.

It is important to note that any of the above-described medical devices may be coated with coatings that comprise drugs, agents or compounds or simply with coatings that contain no drugs, agents or compounds. In addition, the entire medical device may be coated or only a portion of the device may be coated. The coating may be uniform or non-uniform. The coating may be discontinuous. However, the markers on the stent are preferably coated in a manner so as to prevent coating buildup which may interfere with the operation of the device.

In a preferred exemplary embodiment, the self-expanding stents, described above, may be coated with a rapamycin containing polymer. In this embodiment, the polymeric coated stent comprises rapamycin in an amount ranging from about fifty to one-thousand micrograms per square centimeter surface area of the vessel that is spanned by the stent. The rapamycin is mixed with the polyvinylidenefluoride-hexafluoropropylene polymer (described above) in the ratio of drug to polymer of about thirty/seventy. The polymer is made by a batch process using the two monomers, vinylidene fluoride and hexafluoropropylene under high pressure by an emulsion polymerization process. In an alternate exemplary embodiment, the polymer may be made utilizing a batch dispersion process. The polymeric coating weight itself is in the range from about two-hundred to about one thousand seven hundred micrograms per square centimeter surface area of the vessel that is spanned by the stent.

The coated stent comprises a base coat, commonly referred to as a primer layer. The primer layer typically improves the adhesion of the coating layer that comprises the rapamycin. The primer also facilitates uniform wetting of the surface thereby enabling the production of a uniform rapamycin containing coating. The primer layer may be applied using any of the above-described techniques. It is preferably applied utilizing a dip coating process. The primer coating is in the range from about one to about ten percent of the total weight of the coating. The next layer applied is the rapamycin containing layer. The rapamycin containing layer is applied by a spin coating process and subsequently dried in a vacuum oven for approximately sixteen hours at a temperature in the range from about fifty to sixty degrees centigrade. After drying or curing, the stent is mounted onto a stent delivery catheter using a process similar to the uncoated stent. The mounted stent is then packaged and sterilized in any number of ways. In one exemplary embodiment, the stent is sterilized using ethylene oxide.

As described above, various drugs, agents or compounds may be locally delivered via medical devices. For example, rapamycin and heparin may be delivered by a stent to reduce restenosis, inflammation, and coagulation. Various techniques for immobilizing the drugs, agents or compounds are discussed above, however, maintaining the drugs, agents or compounds on the medical devices during delivery and positioning is critical to the success of the procedure or treatment. For example, removal of the drug, agent or compound coating during delivery of the stent can potentially cause failure of the device. For a self-expanding stent, the retraction of the restraining sheath may cause the drugs, agents or compounds to rub off the stent. For a balloon expandable stent, the expansion of the balloon may cause the drugs, agents or compounds to simply delaminate from the stent through contact with the balloon or via expansion. Therefore, prevention of this potential problem is important to have a successful therapeutic medical device, such as a stent.

There are a number of approaches that may be utilized to substantially reduce the above-described concern. In one exemplary embodiment, a lubricant or mold release agent may be utilized. The lubricant or mold release agent may comprise any suitable biocompatible lubricious coating. An exemplary lubricious coating may comprise silicone. In this exemplary embodiment, a solution of the silicone base coating may be introduced onto the balloon surface, onto the polymeric matrix, and/or onto the inner surface of the sheath of a self-expanding stent delivery apparatus and allowed to air cure. Alternately, the silicone based coating may be incorporated into the polymeric matrix. It is important to note, however, that any number of lubricious materials may be utilized, with the basic requirements being that the material be biocompatible, that the material not interfere with the actions/effectiveness of the drugs, agents or compounds and that the material not interfere with the materials utilized to immobilize the drugs, agents or compounds on the medical device. It is also important to note that one or more, or all of the above-described approaches may be utilized in combination.

Figure 22:
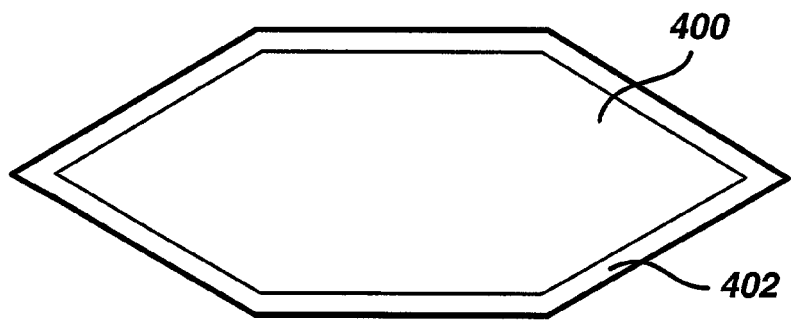
FIG. 22 is a cross-sectional view of a balloon having a lubricious coating affixed thereto in accordance with the present invention.

Referring now to FIG. 22, there is illustrated a balloon 400 of a balloon catheter that may be utilized to expand a stent in situ. As illustrated, the balloon 400 comprises a lubricious coating 402. The lubricious coating 402 functions to minimize or substantially eliminate the adhesion between the balloon 400 and the coating on the medical device. In the exemplary embodiment described above, the lubricious coating 402 would minimize or substantially eliminate the adhesion between the balloon 400 and the heparin or rapamycin coating. The lubricious coating 402 may be attached to and maintained on the balloon 400 in any number of ways including but not limited to dipping, spraying, brushing or spin coating of the coating material from a solution or suspension followed by curing or solvent removal step as needed.

Materials such as synthetic waxes, e.g. diethyleneglycol monostearate, hydrogenated castor oil, oleic acid, stearic acid, zinc stearate, calcium stearate, ethylenebis (stearamide), natural products such as paraffin wax, spermaceti wax, carnuba wax, sodium alginate, ascorbic acid and flour, fluorinated compounds such as perfluoroalkanes, perfluorofafty acids and alcohol, synthetic polymers such as silicones e.g. polydimethylsiloxane, polytetrafluoroethylene, polyfluoroethers, polyalkylglycol e.g. polyethylene glycol waxes, and inorganic materials such as talc, kaolin, mica, and silica may be used to prepare these coatings. Vapor deposition polymerization e.g. parylene-C deposition, or RF-plasma polymerization of perfluoroalkenes and perfluoroalkanes can also be used to prepare these lubricious coatings.

Figure 23:
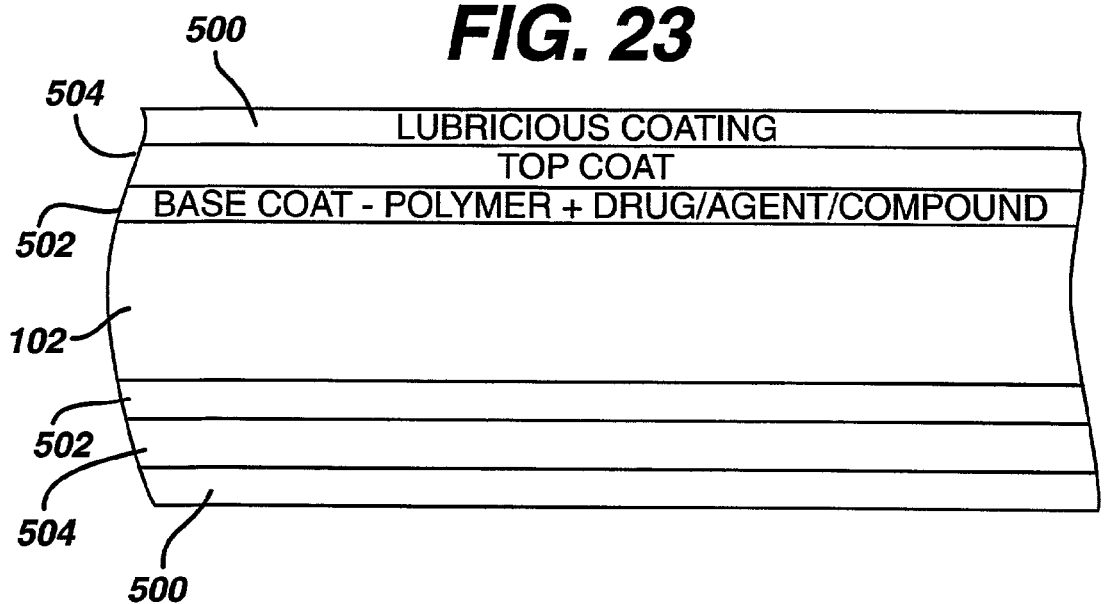
FIG. 23 is a cross-sectional view of a band of the stent in FIG. 1 having a lubricious coating affixed thereto in accordance with the present invention.

FIG. 23 illustrates a cross-section of a band 102 of the stent 100 illustrated in FIG. 1. In this exemplary embodiment, the lubricious coating 500 is immobilized onto the outer surface of the polymeric coating. As described above, the drugs, agents or compounds may be incorporated into a polymeric matrix. The stent band 102 illustrated in FIG. 23 comprises a base coat 502 comprising a polymer and rapamycin and a top coat 504 or diffusion layer 504 also comprising a polymer. The lubricious coating 500 is affixed to the top coat 502 by any suitable means, including but not limited to spraying, brushing, dipping or spin coating of the coating material from a solution or suspension with or without the polymers used to create the top coat, followed by curing or solvent removal step as needed. Vapor deposition polymerization and RF-plasma polymerization may also be used to affix those lubricious coating materials that lend themselves to this deposition method, to the top coating. In an alternate exemplary embodiment, the lubricious coating may be directly incorporated into the polymeric matrix.

Figure 24:
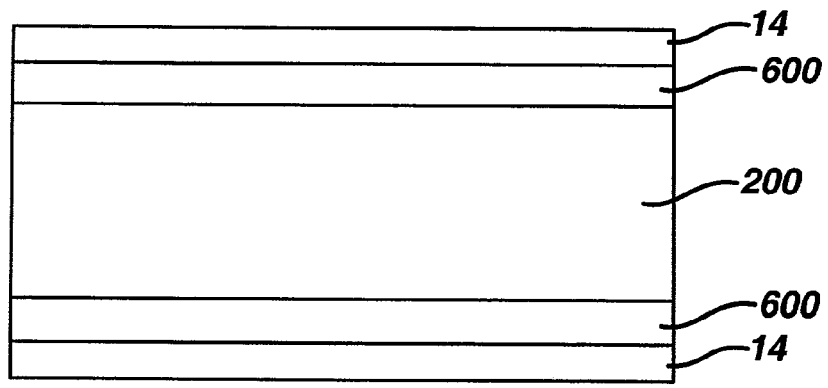
FIG. 24 is a cross-sectional view of a self-expanding stent in a delivery device having a lubricious coating in accordance with the present invention.

If a self-expanding stent is utilized, the lubricious coating may be affixed to the inner surface of the restraining sheath. FIG. 24 illustrates a self-expanding stent 200 (FIG. 10) within the lumen of a delivery apparatus sheath 14. As illustrated, a lubricious coating 600 is affixed to the inner surfaces of the sheath 14. Accordingly, upon deployment of the stent 200, the lubricious coating 600 preferably minimizes or substantially eliminates the adhesion between the sheath 14 and the drug, agent or compound coated stent 200.

Figure 25:
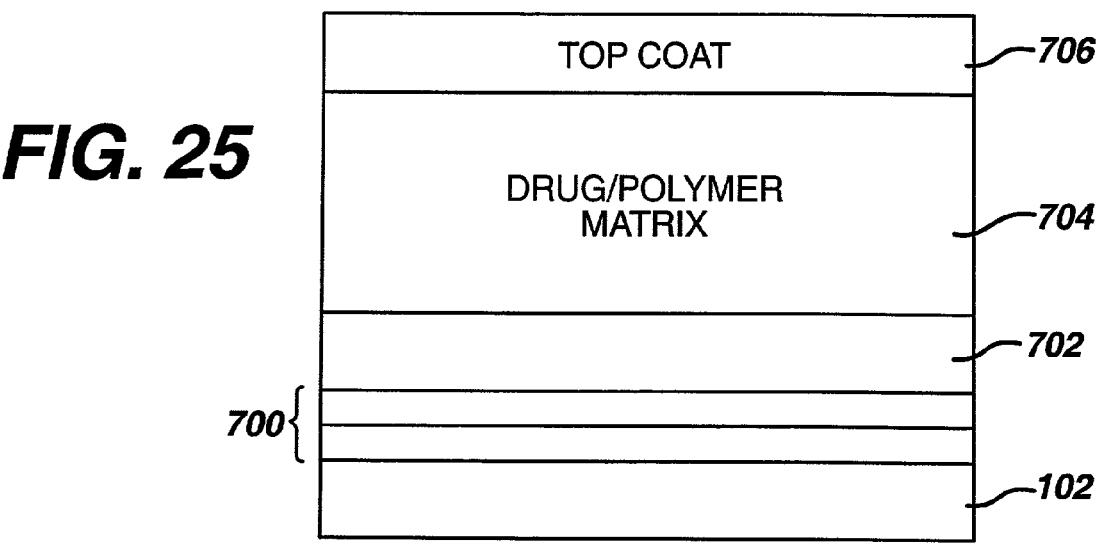
FIG. 25 is a cross-sectional view of a band of the stent in FIG. 1 having a modified polymer coating in accordance with the present invention.

In an alternate approach, physical and/or chemical cross-linking methods may be applied to improve the bond strength between the polymeric coating containing the drugs, agents or compounds and the surface of the medical device or between the polymeric coating containing the drugs, agents or compounds and a primer. Alternately, other primers applied by either traditional coating methods such as dip, spray or spin coating, or by RF-plasma polymerization may also be used to improve bond strength. For example, as shown in FIG. 25, the bond strength can be improved by first depositing a primer layer 700 such as vapor polymerized parylene-C on the device surface, and then placing a second layer 702 which comprises a polymer that is similar in chemical composition to the one or more of the polymers that make up the drug-containing matrix 704, e.g., polyethylene-co-vinyl acetate or polybutyl methacrylate but has been modified to contain cross-linking moieties. This secondary layer 702 is then cross-linked to the primer after exposure to ultraviolet light. It should be noted that anyone familiar with the art would recognize that a similar outcome could be achieved using cross-linking agents that are activated by heat with or without the presence of an activating agent. The drug-containing matrix 704 is then layered onto the secondary layer 702 using a solvent that swells, in part or wholly, the secondary layer 702. This promotes the entrainment of polymer chains from the matrix into the secondary layer 702 and conversely from the secondary layer 702 into the drug-containing matrix 704. Upon removal of the solvent from the coated layers, an interpenetrating or interlocking network of the polymer chains is formed between the layers thereby increasing the adhesion strength between them. A top coat 706 is used as described above.

A related difficulty occurs in medical devices such as stents. In the drug-coated stents crimped state, some struts come into contact with each other and when the stent is expanded, the motion causes the polymeric coating comprising the drugs, agents or compounds to stick and stretch. This action may potentially cause the coating to separate from the stent in certain areas. The predominant mechanism of the coating self-adhesion is believed to be due to mechanical forces. When the polymer comes in contact with itself, its chains can tangle causing the mechanical bond, similar to hook and loop fasteners such as Velcro®. Certain polymers do not bond with each other, for example, fluoropolymers. For other polymers, however, powders may be utilized. In other words, a powder may be applied to the one or more polymers incorporating the drugs, agents or other compounds on the surfaces of the medical device to reduce the mechanical bond. Any suitable biocompatible material which does not interfere with the drugs, agents, compounds or materials utilized to immobilize the drugs, agents or compounds onto the medical device may be utilized. For example, a dusting with a water soluble powder may reduce the tackiness of the coatings surface and this will prevent the polymer from sticking to itself thereby reducing the potential for delamination. The powder should be water- soluble so that it does not present an emboli risk. The powder may comprise an anti-oxidant, such as vitamin C, or it may comprise an anti-coagulant, such as aspirin or heparin. An advantage of utilizing an anti-oxidant may be in the fact that the anti-oxidant may preserve the other drugs, agents or compounds over longer periods of time.

It is important to note that crystalline polymers are generally not sticky or tacky. Accordingly, if crystalline polymers are utilized rather than amorphous polymers, then additional materials may not be necessary. It is also important to note that polymeric coatings without drugs, agents, and/or compounds may improve the operating characteristics of the medical device. For example, the mechanical properties of the medical device may be improved by a polymeric coating, with or without drugs, agents and/or compounds. A coated stent may have improved flexibility and increased durability. In addition, the polymeric coating may substantially reduce or eliminate galvanic corrosion between the different metals comprising the medical device.

Any of the above-described medical devices may be utilized for the local delivery of drugs, agents and/or compounds to other areas, not immediately around the device itself. In order to avoid the potential complications associated with systemic drug delivery, the medical devices of the present invention may be utilized to deliver therapeutic agents to areas adjacent to the medical device. For example, a rapamycin coated stent may deliver the rapamycin to the tissues surrounding the stent as well as areas upstream of the stent and downstream of the stent. The degree of tissue penetration depends on a number of factors, including the drug, agent or compound, the concentrations of the drug and the release rate of the agent.

The drug, agent and/or compound/carrier or vehicle compositions described above may be formulated in a number of ways. For example, they may be formulated utilizing additional components or constituents, including a variety of excipient agents and/or formulary components to affect manufacturability, coating integrity, sterilizability, drug stability, and drug release rate. Within exemplary embodiments of the present invention, excipient agents and/or formulary components may be added to achieve both fast-release and sustained-release drug elution profiles. Such excipient agents may include salts and/or inorganic compounds such as acids/bases or buffer components, anti-oxidants, surfactants, polypeptides, proteins, carbohydrates including sucrose, glucose or dextrose, chelating agents such as EDTA, glutathione or other excipients or agents.

In the above described exemplary embodiments, the focus is on the local delivery of drugs, agents and/or compounds for the treatment of restenosis and restenosis related vascular disease and the devices used therefor. In the exemplary embodiments described below, the focus is on a different type of vascular disease, namely, vulnerable plaque. Accordingly, exemplary devices and drugs, agents and/or compounds for the treatment of vulnerable plaque are described and illustrated in detail below.

Atherosclerosis is a thickening and hardening of the arteries and is generally believed to be caused by the progressive buildup of fatty substances, e.g. cholesterol, cellular waste products, inflammatory cells, calcium and other substances in the inner lining or intima of the arteries. The buildup of these substances may in turn stimulate cells in the walls of the affected arteries to produce additional substances that result in the further buildup of cells.

Atherosclerosis is a slow, complex disease that typically starts in childhood and progresses as the individual ages. The rate of progression may be affected by a number of factors, including blood cholesterol levels, diabetes, obesity, physical inactivity, high blood pressure and tobacco use. This buildup in commonly referred to as plaque and may grow large enough to significantly reduce blood flow through the affected arteries.

Essentially, the deposits of the various substances set forth above, and the proliferation of additional cellular substances or constituents caused thereby, substantially enlarge the intima, which in turn reduces luminal cross-sectional area and decreases the diameter of the affected artery or arteries, which in turn reduces the oxygen supply to one or more organs. The deposits or plaque may also rupture and form blood clots or thrombi that can completely obstruct blood flow in the affected artery or break free and travel, emboli, to another part of the body. If either of these events occur, the individual may suffer a myocardial infarction if the artery or arteries affected perfuse the heart or a stroke if the artery or arteries affected supply blood to the brain. If the artery or arteries affected supply blood to a limb or appendage, gangrene may result.

As indicated above, conventional wisdom holds that heart attacks, for example, originate from severe blockages created by atherosclerosis. The increase of lipids in the artery or arteries and ensuing tissue reaction lead to a narrowing of the affected artery or arteries, which in turn, may result in angina and eventually coronary occlusion, sudden cardiac death and thrombotic stroke. Relatively recent research, however, is leading to a shift in understanding atherosclerosis. Researchers now believe that at least some coronary artery disease is an inflammatory process, in which inflammation causes plaque buildup or progression and rupture. These plaques which are prone to rupture, commonly referred to as vulnerable plaques, do not block flow in the affected artery or arteries per se, but rather, much like an abscess, they may be ingrained in the arterial wall so that they are difficult to detect. Essentially, these vulnerable plaques cannot be seen by conventional angiography and/or fluoroscopy, and they do not typically cause symptoms such as shortness of breath or pain. Techniques for determining the presence of vulnerable plaques are, however, improving as discussed subsequently.

For a variety of reasons, these so-called vulnerable plaques are more likely to erode or rupture, creating emboli and raw or exposed tissue surfaces that are highly thrombogenic. Accordingly, it is now accepted that the majority of cases of acute myocardial infarction, sudden cardiac death and thrombolitic stroke result from the disruption of vulnerable atherosclerotic plaques leading to thrombosis. Therefore, these vulnerable plaques are more dangerous than other plaques that simply cause pain, and may be responsible for as much as sixty to eighty percent of all heart attacks.

More specifically, unstable or vulnerable plaques are inflammatory vascular lesions that develop in atherosclerotic blood vessels. Vulnerable plaques are characterized by active inflammation, cellular hyperplasia and variable degrees of lumen obstruction. Morphologically, vulnerable plaques comprise a fibrous cap in contact with the lumen of the vessel overlying a core of lipid and cellular material. Vulnerable plaque lesions are not typically obstructive, in contrast to chronic stable plaques that produce ischemic symptoms. For that reason, they are not easily detected.

The hallmark of vulnerable plaques is active inflammation with significant inflammatory cell infiltration, predominantly T-lymphocytes and macrophage, causing the generation of proteolytic enzymes that essentially digest the wall of the fibrous cap thereby inducing plaque instability and eventually plaque rupture. Plaque rupture exposes highly thrombogenic material in the lipid core to flowing blood leading to the rapid development of occlusive thrombi. Ruptured vulnerable plaque, as stated above, is the primary cause of acute coronary and cerebral syndromes. These include unstable angina, myocardial infarction, both Q-wave and non-Q-wave myocardial infarction, cerebral stroke and transient cerebral ischemia. In other words, ruptured vulnerable plaque accounts for a significant percentage of cardiovascular morbidity and mortality.

Given the lack of currently available effective technologies for detecting vulnerable plaque, the treatment of vulnerable plaque is typically initiated only after the plaque has ruptured and clinical symptoms have developed. Detection technologies currently under investigation include refined magnetic resonance imaging, thermal sensors that measure the temperature of the arterial wall on the premise that the inflammatory process generates heat, elasticity sensors, intravascular ultrasound, optical coherence tomography, contrast agents, and near-infrared and infrared light. As better diagnostic methods evolve to identify vulnerable plaque lesions before they rupture, it becomes possible to treat discrete lesions before dangerous clinical symptoms occur. The treatment of vulnerable plaque, however, is preferably as described below.

Essentially, there are two physiologic processes ongoing in active vulnerable plaque, inflammation and lipid metabolism. Inflammation is an ongoing process which includes the inflammation of the fibrous cap and creating a cap vulnerable to rupture. Lipid metabolism is the formation of a molten or active lipid pool or core comprising a paliable, cholesterolemic lipid material susceptible to rupture. The inflammation process is the acute phase and the lipid metabolism is the chronic phase of vulnerable plaque disease.

A stent or other scaffold structure designed to maintain vessel patentcy and comprising a multilaminate coating architecture, including one or more therapeutic agents, drugs, and/or compounds for treating both the inflammation and lipid metabolism processes, may be utilized to effectively treat vulnerable plaques. In one exemplary embodiment, a stent comprising a coating having a two tier release profile may be utilized to treat both the acute and chronic phases of vulnerable plaque. For example, antiinflammatory therapeutic agents, such as corticosteroids, non-steroidal antiinflammatories, acetylsalicyclic acid, acetaminophen and ibuprofen may be incorporated into the coating architecture for "fast release" and shorter overall duration to address the acute phase of vulnerable plaque disease and lipid lowering or lipid modifying agents may be incorporated into the coating architecture for "slow release" and longer overall duration to address the chronic phase of vulnerable plaque disease. The entire stent/drug, agent and/or compound architecture may be released utilizing a variety of non-resorbable or resorbable polymers to control, modulate and/or optimize the delivery profile for optimal physiologic effect. In other words, specific therapeutic drug, agent and/or compound delivery profiles may be utilized in conjunction with the stent to treat all aspects of vulnerable plaques, for example, fast release antiinflammatory drugs, agents and/or compounds to address the inflammatory rupture of the fibrous cap and slow release lipid lowering or lipid modifying drugs, agents and/or compounds to affect the size and composition of the vulnerable plaque lipid pool.

The stent may comprise any suitable scaffold structure, including balloon expandable stents, an exemplary embodiment of which is illustrated in FIG. 26, constructed from stainless steel or other metal alloys, and/or self-expanding stents, an exemplary embodiment of which is illustrated in FIG. 10, constructed from nitinol or other shape memory metal alloys. Alternately, the stent may be made from non-metallic materials, such as ceramics and/or polymers, which may be biodegradable. The biodegradable stent would serve as a temporary scaffold and eventually dissolve over a period of time raging from days or weeks to months and years. The stent would be mounted on a delivery catheter and delivered percutaneously through the lumen of a blood vessel to the site of the vulnerable plaque lesion as described in detail above with respect to treating restenosis. The stent, as described above, is designed to maintain vessel patency and also provide structural support to the weakened or potentially weakened fibrous cap and prevent it from rupturing. The stent also provides a means for preventing further encroachment by the lesion.

The one or more therapeutic drugs, agents and/or compounds utilized in combination with the stent would preferably prevent neointimal hyperplasia that is commonly encountered in stenting and which could lead to restenosis and device failure as described in detail above. In addition, the same or additional therapeutic drugs, agents and/or compounds would preferably stabilize or passivate the lesion by reducing local inflammation and preventing further erosion of the fibrous cap. The one or more therapeutic drugs, agents and/or compounds may be delivered in a polymer matrix coating applied to the stent struts or embedded into the material forming the stent itself and would release into the vessel wall over a predetermined period of time, preferably utilizing the dual profile release rate as briefly described above.

Figure 27:
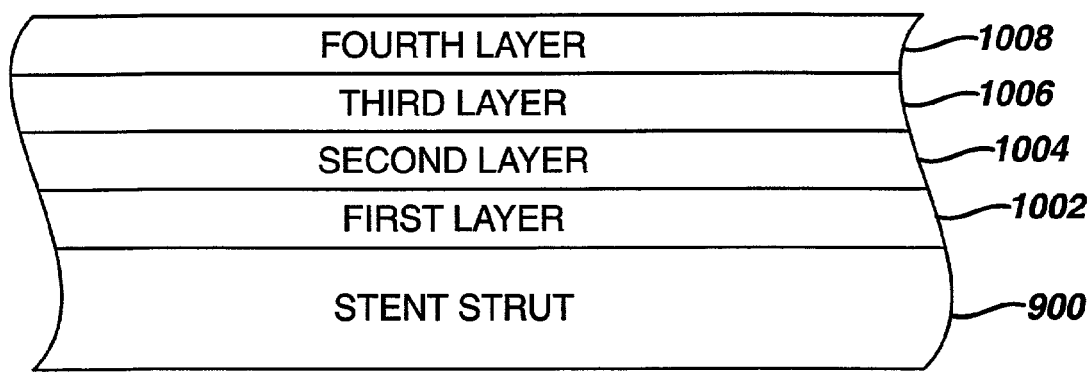
FIG. 27 is a cross-sectional view of a band of the stent of FIG. 26 having multiple polymer layers, some of which comprise therapeutic dosages of drugs, agents and/or compounds, for treating vulnerable plaque in accordance with a first exemplary embodiment of the invention.

As stated above, any type of stent may be utilized; however, for ease of explanation, one type of stent is described. In one exemplary embodiment, the balloon expandable stent illustrated in FIG. 26 may comprise one or more therapeutic drugs, agents and/or compounds incorporated into a polymeric matrix for the treatment of vulnerable plaque. The drug, agent and/or compound/polymeric matrix may be applied utilizing any of the techniques and methodologies described above. FIG. 27 is a cross-sectional view of a strut or member of the stent 900, illustrated in FIG. 26, having therapeutic dosages of one or more drugs, agents and/or compounds for the treatment of vulnerable plaque thereon. As described in detail above, various polymers and combinations of polymers in various configurations may be utilized as a vehicle for the delivery of the one or more therapeutic agents. In the exemplary embodiment illustrated in FIG. 27, a first polymer layer 1002 comprises a solution of poly(ethylene-co-vinylacetate) and polybutylmethacrylate. A slow release lipid lowering or lipid modifying drug, agent and/or compound in therapeutic dosages may be incorporated into this first polymer layer 1002. This lipid lowering or lipid modifying drug, agent and/or compound may comprise any suitable therapeutic drug, agent, and/or compound including HMG co-enzyme reductase inhibitors or statins and lipid transporting agents. The selection of polymers should preferably be compatible with the particular therapeutic drug(s), agent(s) and/or compound(s). A second polymer layer 1004 comprising only polybutylmethacrylate and no therapeutic drug, agent and/or compound may be utilized as a diffusion barrier to control the release rate of the lipid lowering agent. The thickness of the second polymer layer 1004 may be utilized to determine the rate at which the lipid lowering drug, agent and/or compound elutes from the coated stent 900. In an alternate exemplary embodiment, a single layer may be utilized. For example, no diffusion barrier would be necessary as in the case with the fluoropolymers described above. As described above, the one or more drugs, agents and/or compounds elute from the polymer matrix by diffusion therethrough. Polymers are permeable, thereby allowing solids, liquids and gases to escape therefrom. A third polymeric layer 1006 comprises a solution of poly(ethylene-co-vinylacetate) and polybutylmethacrylate and one or more therapeutic drugs, agents and/or compounds for treating the inflammatory process contribution to vulnerable plaque rupture. Although this third polymer layer 1006 is described as comprising the same polymers as the first polymer layer 1002, different or additional polymers may be utilized. In this third polymer layer 1006, one or more of the above-described antiproliferatives, antiinflammatories and antithrombotics may be utilized. In addition, plaque stabilizers may also be utilized in this third layer 1006.

Any number of antiproliferatives may be utilized in the third layer 1006. For example, rapamycin or any analog or derivative of rapamycin, that binds to FKBP12 and inhibits TOR, a direct inhibitor of the TOR kinase, a taxane such as paclitaxel or a taxane derivative that inhibits microtubule function, a cyclin dependent kinase inhibitor that will block the cell cycle, retinoid such as tretinoin, a growth factor receptor kinase inhibitor such as RWJ 540973 or a farnesyl transferase inhibitor such as R115,777. As is the case with antiproliferatives, any number of antiinflammatories may be utilized in the third layer 1006. For example, rapamycin, steroids such as dexamethasone or other corticosteroids, a P38 MAP kinase inhibitor, an antagonist of tumor necrosis factor, a mast cell stabilizer, an antioxidant to prevent lipid peroxidation such as probucol or AGI-1067. The plaque stabilizer may include a protease inhibitor, including a matrix metalloprotease (MMP) inhibitor, either specific for a particular MMP, for example MMP2 or MMP9 or a non-specific MMP inhibitor, an inhibitor of the compliment cascade, an anti-apoptotic agent such as a BCL2 inhibitor or a caspase inhibitor, a TGFbeta agonist or mimetic to promote cap strengthening, and/or a vitronectin (Av/B3) antagonist. A fourth polymer layer 1008 comprising only polybutylmethacrylate and no therapeutic drug, agent and/or compound may be used as a diffusion barrier to control the release rate of the therapeutic agents for treating the inflammatory process contribution to vulnerable plaque. Although this fourth polymer layer 1008 is described as comprising the same polymer as the second polymer layer 1004, different or additional polymers may be utilized. In an alternate exemplary embodiment, a single layer may be utilized.

Figure 28:
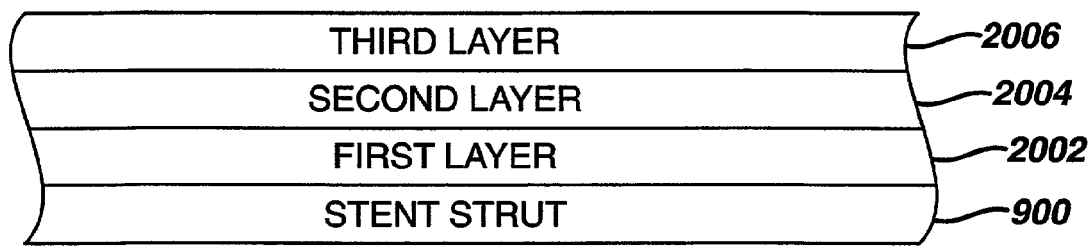
FIG. 28 is a cross-sectional view of a band of the stent of FIG. 27 having multiple polymer layers, some of which comprise therapeutic dosages of drugs, agents and/or compounds, for treating vulnerable plaque in accordance with a second exemplary embodiment of the invention.

In the above-described exemplary embodiment, four independent layers 1002, 1004, 1006 and 1008 are disclosed; however, it is important to note that more or less layers may be utilized. For example, as illustrated in FIG. 28, a three layer structure may be utilized. In this exemplary embodiment, the first polymer layer 2002 may be identical to the first polymer layer 1002 illustrated in FIG. 27, the second polymer layer 2004 may be identical to the third polymer layer 1006 illustrated in FIG. 27, and the third polymer layer 2006 may be identical to the second polymer layer 1004 or fourth polymer layer 1008 illustrated in FIG. 27. In other words, a single diffusion layer may be utilized to control the release rate of the one or more therapeutic drugs, agents and/or compounds. Essentially, depending on the polymers utilized as well as the specific drugs, agents and/or compounds, a single layer may be capable of delivering different drugs, agents and/or compounds at different rates thereby addressing both the acute and chronic phases of vulnerable plaque disease.

It is important to note that a wide variety of different drugs, agents and/or compounds may be utilized alone or in combination to treat both processes in vulnerable plaque rupture. In addition, any number of biocompatible polymers may also be utilized. In order to achieve the best results, it is preferable that the whole polymeric matrix be designed such that the release of one or more drugs, agents and/or compounds for treating the lipid pool be released at a slow rate and for a long duration, preferably in the range from about zero days to about twelve months or longer, and the one or more drugs, agents and/or compounds for treating the inflammatory process be released at a relatively fast rate and shorter duration, preferably in the range from about zero days to about thirty days.

It is important to note that rapamycin itself may be beneficial in the treatment of both the acute and chronic phases of vulnerable plaque disease. In addition, the systemic delivery of one or more drugs, agents and/or compounds in conjunction with the local delivery may also be useful as described above with respect to restenosis.

As stated above, a single drug such as rapamycin may be utilized in the treatment of both the acute and chronic phases of vulnerable plaque disease. Other drugs, agents or compounds, such as HMG co-enzyme reductase inhibitors may also be utilized to treat both phases of the disease. Heparin may also be incorporated into the polymeric matrix. Heparin, as well as other thrombolytics or antithrombotics may be utilized to treat secondary effects of thrombus formation upon exposure of the lipid pool to blood in the event of rupture. These antithrombotics or thrombolytic drugs would also be part of the chronic phase of treatment.

In addition to the various drugs, agents and/or compounds described above, the coating technology may, as described above, be created or developed such that a single coating layer with barrier coat releases the therapeutic drugs, agents and/or compounds with different kinetics. Also, the barrier coat does not need to be a polymer. Rather, the barrier coat may comprise a surface treatment such as a chemical modification, e.g. oxygenation.

As described above, a stent or other scaffold may be positioned at the lesion site; however, other positions may be more advantageous. For example, if the plaque is "highly" vulnerable, the coated stent may be positioned proximal to the treatment site, since stenting of the lesion may aggravate the condition rather than treat or mitigate the condition. In one exemplary embodiment, the location or placement of the stent would be primarily proximal to the lesion, with the potential for treatment of several distal lesions, either in the same conduit or tributaries thereof.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An intraluminal medical device for the treatment of atherosclerotic vulnerable plaque comprising:
   a stent configured to provide structural support for a fibrous cap of a vulnerable plaque lesion;
   a biocompatible vehicle affixed to at least a portion of the stent, the biocompatible vehicle including at least one layer in direct contact with the internal surface of a vessel in which the stent is positioned;
   at least one first agent in a therapeutic dosage incorporated into the biocompatible vehicle for treating the inflammation associated with the acute phase of the vulnerable plaque lesion;
   at least one second agent in a therapeutic dosage incorporated into the biocompatible vehicle for treating the lipid core associated with the chronic phase of the vulnerable plaque lesion, the biocompatible vehicle being configured to release the at least one first agent faster than the at least one second agent and configured to release the at least one first agent for a shorter duration than the at least one second agent; at least one third agent in a therapeutic dosage incorporated into the biocompatible vehicle for preventing neointimal hyperplasia caused by the placement of the stent.

2. The intraluminal medical device for the treatment of atherosclerotic vulnerable plaque according to claim 1, wherein the stent is balloon expandable.

3. The intraluminal medical device for the treatment of atherosclerotic vulnerable plaque according to claim 1, wherein the stent is self-expanding.

4. The intraluminal medical device for the treatment of atherosclerotic vulnerable plaque according to claim 1, wherein the biocompatible vehicle comprises a polymeric coating.

5. The intraluminal medical device for the treatment of atherosclerotic vulnerable plaque according to claim 4, wherein the polymeric coating comprises at least one layer configured to release the at least one first agent faster than the at least one second agent and to release the at least one first agent for a shorter duration than the at least one second agent.

6. The intraluminal medical device for the treatment of atherosclerotic vulnerable plaque according to claim 5, wherein the at least one first agent comprises an anti-inflammatory/inflammation blocking agent.

7. The intraluminal medical device, for the treatment of atherosclerotic vulnerable plaque according to claim 5, wherein the at least one first agent comprises an anti-proliferative agent.

8. The intraluminal medical device for the treatment of atherosclerotic vulnerable plaque according to claim 5, wherein the at least one first agent comprises an anti-thrombogenic agent.

9. The intraluminal medical device for the treatment of atherosclerotic vulnerable plaque according to claim 5, wherein the at least one first agent comprises rapamycin.

10. The intraluminal medical device for the treatment of atherosclerotic vulnerable plaque according to claim 5, wherein the at least one first agent comprises dexamethasone.

11. The intraluminal medical device for the treatment of atherosclerotic vulnerable plaque according to claim 5, wherein the at least one first agent comprises anti-inflammatory corticosteroids.

12. The intraluminal medical device for the treatment of atherosclerotic vulnerable plaque according to claim 5, wherein the at least one first agent comprises rapamycin derivatives.

13. The intraluminal medical device for the treatment of atherosclerotic vulnerable plaque according to claim 5 wherein the at least one first agent comprises rapamycin analogs.

14. The intraluminal medical device for the treatment of atherosclerotic vulnerable plaque according to claim 5 wherein the at least one first agent comprises a direct inhibitor of the target of rapamycin kinase (mTOR).

15. The intraluminal medical device for the treatment of atherosclerotic vulnerable plaque according to claim 5 wherein the at least one first agent comprises a taxane, including paclitaxel and a taxane derivative that inhibits microtubule function.

16. The intraluminal medical device for the treatment of atherosclerotic vulnerable plaque according to claim 5 wherein the at least one first agent comprises a cyclin dependent kinase inhibitor that will block the cell cycle.

17. The intraluminal medical device for the treatment of atherosclerotic vulnerable plaque according to claim 5 wherein the at least one first agent comprises a retinoid.

18. The intraluminal medical device for the treatment of atherosclerotic vulnerable plaque according to claim 5 wherein the at least one first agent comprises a growth factor receptor kinase inhibitor.

19. The intraluminal medical device for the treatment of atherosclerotic vulnerable plaque according to claim 5 wherein the at least one first agent comprises a farnesyl transferase inhibitor.

20. The intraluminal medical device for the treatment of atherosclerotic vulnerable plaque according to claim 5 wherein the at least one first agent comprises a P38 MAP kinase inhibitor.

21. The intraluminal medical device for the treatment of atherosclerotic vulnerable plaque according to claim 5 wherein the at least one first agent comprises an antagonist of tumor necrosis factor.

22. The intraluminal medical device for the treatment of atherosclerotic vulnerable plaque according to claim 5 wherein the at least one first agent comprises a mast cell stabilizer.

23. The intraluminal medical device for the treatment of atherosclerotic vulnerable plaque according to claim 5 wherein the at least one first agent comprises an antioxidant.

24. The intraluminal medical device for the treatment of atherosclerotic vulnerable plaque according to claim 5, wherein the at least one second agent comprises a lipid lowering agent.

25. The intraluminal medical device for the treatment of atherosclerotic vulnerable plaque according to claim 24, wherein the lipid lowering agent is an HMG co-enzyme reductase inhibitor or statin.

26. The intraluminal medical device for the treatment of atherosclerotic vulnerable plaque according to claim 24, wherein the lipid lowering agent comprises rapamycin.

27. The intraluminal medical device for the treatment of atherosclerotic vulnerable plaque according to claim 5, wherein the at least one second agent comprises a protease inhibitor including a matrix metalloprotease inhibitor.

28. The intraluminal medical device for the treatment of atherosclerotic vulnerable plaque according to claim 5, wherein the at least one second agent comprises an antiapoptotic agent.

29. The intraluminal medical device for the treatment of atherosclerotic vulnerable plaque according to claim 5, wherein the at least one second agent comprises a TGFbeta agonist.

30. The intraluminal medical device for the treatment of atherosclerotic vulnerable plaque according to claim 5, wherein the at least one second agent comprises a vitronectin antagonist.

* * * * *